(12) United States Patent
Worm

(10) Patent No.: US 7,915,401 B2
(45) Date of Patent: Mar. 29, 2011

(54) COMPOUNDS FOR THE MODULATION OF BETA-CATENIN EXPRESSION

(75) Inventor: Jesper Worm, Copenhagen V (DK)

(73) Assignees: Enzon Pharmaceuticals, Inc., Bridgewater, NJ (US); Santaris Pharma A/S, Horsholm (DK)

(*) Notice: Subject to any disclaimer, the term of this patent is extended or adjusted under 35 U.S.C. 154(b) by 13 days.

(21) Appl. No.: 12/356,923

(22) Filed: Jan. 21, 2009

(65) Prior Publication Data

US 2009/0203137 A1    Aug. 13, 2009

Related U.S. Application Data

(63) Continuation of application No. 12/113,031, filed on Apr. 30, 2008, now abandoned.

(60) Provisional application No. 61/023,244, filed on Jan. 24, 2008, provisional application No. 60/915,371, filed on May 1, 2007.

(51) Int. Cl.
C07H 21/04 (2006.01)
A61K 48/00 (2006.01)

(52) U.S. Cl. .............. 536/24.5; 536/23.1; 536/24.3; 536/24.31; 536/24.33; 514/44

(58) Field of Classification Search .................. None
See application file for complete search history.

(56) References Cited

U.S. PATENT DOCUMENTS

| | | | |
|---|---|---|---|
| 4,914,210 A | 4/1990 | Levenson et al. | |
| 4,962,029 A | 10/1990 | Levenson et al. | |
| 6,066,500 A * | 5/2000 | Bennett et al. | 435/375 |
| 7,087,229 B2 | 8/2006 | Zhao et al. | |
| 2003/0064384 A1 | 4/2003 | Hung et al. | |
| 2004/0235773 A1 | 11/2004 | Zhao et al. | |
| 2009/0005335 A1 | 1/2009 | Worm | |

FOREIGN PATENT DOCUMENTS

| | | |
|---|---|---|
| EP | 1222309 B1 | 12/2005 |
| WO | 01/00872 | 1/2001 |
| WO | WO2004/046160 A2 | 6/2004 |
| WO | WO2007/031081 A2 | 3/2007 |
| WO | WO2007/031091 A2 | 3/2007 |
| WO | WO2007/146511 A2 | 12/2007 |
| WO | WO2008/034123 A2 | 3/2008 |
| WO | WO2008/053314 A2 | 5/2008 |

OTHER PUBLICATIONS

Veeramachanemi N.K. et al.: "Down-regulation of beta catenin inhibits the growth of esophageal carcinoma cells". The Journal of Thoracic and Cardiovascular Surgery, vol. 127, pp. 92-98, Jan. 2004.
Roh H. et al.: "Suppression of beta-catenin inhibits the neoplastic growth of APC-mutant colon cancer cells". Cancer Research, vol. 61, pp. 6563-6568, Sep. 1, 2001.
Canter R.J. et al.: "Suppression of beta-catenin by antisense oligomers augments tumor response to isolated limb perfusion in a rodent model of adenomatous polyposis coli-mutant colon cancer". Annals of Surgical Oncology, vol. 12, No. 9, pp. 733-742, Sep. 1, 2005.
Green D.W. et al.: "Beta-catenin antisense treatment decreases beta-catenin expression and tumor growth rate in colon carcinoma xenografts" Journal of Surgical Research, vol. 101, pp. 16-20, 2001.
Emanuele S. et al.: "Sodium Butyrate induces apoptosis in human epatoma cells by a mitochondrial/caspase pathway, associated with degradation of beta-catenin, PRb and Bcl-XL" European Journal of Cancer, vol. 40, pp. 1441-1452, 2004.
Li M. et al.: "Antitumor activity and chemosensitization effects of novel antisense oligonucleotides targeting beta-catenin". Proceedings of the American Association for Cancer Research Annual Meeting, vol. 46, p. 137, Apr. 2005.
Heasman J. et al.: "Overexpression of Cadherins and underexpression of beta-catenin inhibit dorsal mesoderm induction in early Xenopus embryos". Cell, vol. 79, No. 5, pp. 791-803, Dec. 1994.
Kim K. et al.: "Tissue-specific expression of beta-catenin in normal mesenchyme and uveal melanomas and its effect on invasiveness". Experimental Cell Research, vol. 245, pp. 79-90, Jan. 1998.
International Preliminary Report on Patentability and Written Opinion issued in PCT/EP2008/055365 and dated Nov. 3, 2009.
International Search Report issued in PCT/EP2008/055365 and dated May 7, 2009.
Christensen, et al., "Intercalating nucleic acids containing insertions of 1-O-(1-pyrenylmethyl)glycerol: stabilisation of dsDNA and discrimination of DNA over RNA," Nucleic Acids Research, vol. 30, No. 22, pp. 4918-4925 (2002).
de La Coste, et al., "Somatic mutations of the β-catenin gene are frequent in mouse and human hepatocellular carcinomas," Proc. Natl. Acad. Sci. USA, vol. 95, pp. 8847-8851 (1998).
Freier, et al., "The ups and downs of nucleic acid duplex stability: structure-stability studies on chemically-modified DNA:RNA duplexes," Nucleic Acids Research, vol. 25, No. 22, pp. 4429-4443 (1997).
Manoharan, et al., "Novel Functionalization of the Sugar Moiety of Nucleic Acids for Multiple Labeling in the Minor Groove," Tetrahedron Letters, vol. 32, No. 49, pp. 7171-7174 (1991).
Morin, et al., Activation of β-Catenin-Tcf Signaling in Colon Cancer by Mutation in β-Catenin or APC, Science, vol. 275, pp. 1787-1790 (1997).
U.S. Appl. No. 60/915,371, filed May 1, 2007.
U.S. Appl. No. 60/977,409.
U.S. Appl. No. 61/023,244, filed Jan. 24, 2008.
Powell, et al., "APC mutations occur early during colorectal tumorigenesis," Nature, vol. 359, p. 235-237 (1992).
Rubinfeld, et al., "Stabilization on β-Catenin by Genetic Defects in Melanoma Cell Lines," Science, vol. 275, p. 1790-1792 (1997).
Sparks, et al., "Mutational Analysis of the APC/β-Catenin-Tcf Pathway in Colorectal Cancer," Cancer Research, Vo. 58, pp. 1130-1134 (1998).

(Continued)

Primary Examiner — Amy Bowman
(74) Attorney, Agent, or Firm — Lucas & Mercanti, LLP

(57) ABSTRACT

The invention relates to oligomer compounds (oligomers), which target beta-catenin mRNA in a cell, leading to reduced expression of beta-catenin. Reduction of beta-catenin expression is beneficial for a range of medical disorders, such as hyperproliferative disorders, such as cancer. The invention provides therapeutic compositions comprising oligomers and methods for modulating the expression of beta-catenin using said oligomers, including methods of treatment.

5 Claims, 8 Drawing Sheets

OTHER PUBLICATIONS

Figure 2:
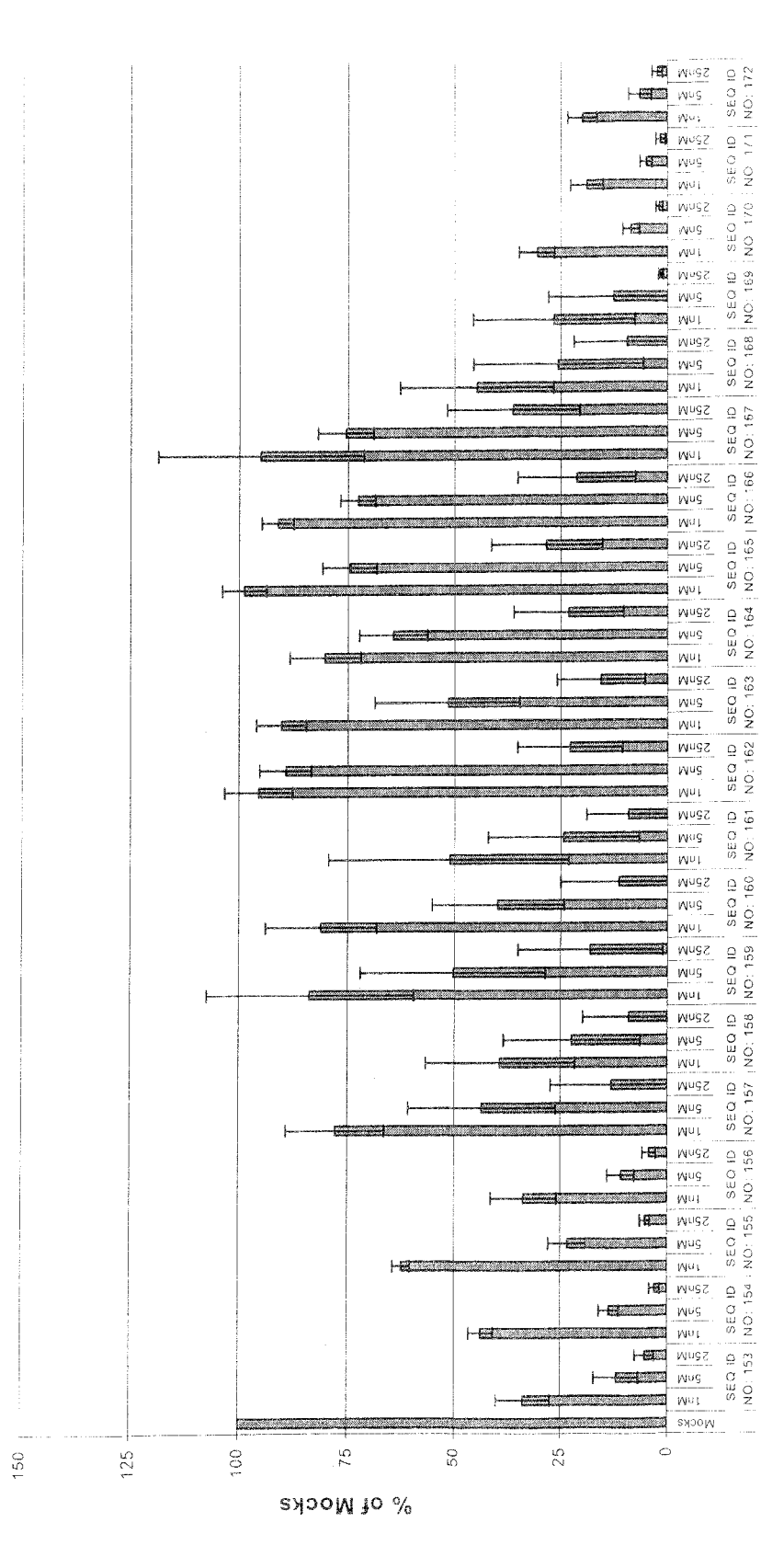

Uhlmann, "Recent advances in the medicinal chemistry of antisense oligonucleotides," *Current Opinion in Drug Discovery & Development*, vol. 3, No. 2, pp. 203-213 (2000).

Zhao, et al., "Delivery of G3139 using releasable PEG-linkers: Impact on pharmacokinetic profile and anti-tumor efficacy," *Journal of Controlled Release*, vol. 119, pp. 143-152 (2007).

Zhao, et al., "A New Platform for Oligonucleotide Delivery Utilizing the PEG Prodrug Approach," *Bioconjugate Chem.*, vol. 16, pp. 758-766 (2005).

Zhang, Y. et al., In vitro and in vivo characterization of two novel beta-catenin RNA antagonists, EZN-3889 and EZN-3892. Enzon Pharmaceuticals, Inc. AACR Poster, Washington, D.C. 2010.

Xu et al., Effective small interfering RNAs and phosphorothioate antisense DNAs have different preferences for target sites in the luciferase mRNAs. Biochemical and Biophysical Research Communications, May 2003, 306, pp. 712-717.

* cited by examiner

Figure 1

```
   1 cccacgcgtc cgggcagcag cgttggcccg gccccgggag cggagagcga ggggaggcgg
  61 agacggagga aggtctgagg agcagcttca gtccccgccg agccgccacc gcaggtcgag
 121 gacggtcgga ctcccgcggc gggaggagcc tgttcccctg agggtatttg aagtatacca
 181 tacaactgtt ttgaaaatcc agcgtggaca atggctactc aagctgattt gatggagttg
 241 gacatggcca tggaaccaga cagaaaagcg gctgttagtc actggcagca acagtcttac
 301 ctggactctg gaatccattc tggtgccact accacagctc ttctctgag tggtaaaggc
 361 aatcctgagg aagaggatgt ggatacctcc caagtcctgt atgagtggga cagggattt
 421 tctcagtcct tcactcaaga acaagtagct gatattgatg gacagtatgc aatgactcga
 481 gctcagaggg tacgagctgc tatgttccct gagacattag atgagggcat gcagatccca
 541 tctacacagt ttgatgctgc tcatcccact aatgtccagc gtttggctga accatcacag
 601 atgctgaaac atgcagttgt aaacttgatt aactatcaag atgatgcaga acttgccaca
 661 cgtgcaatcc ctgaactgac aaaactgcta aatgacgagg accaggtggt ggttaataag
                    SEQ ID NO: 1
 721 gctgcagtta tggtccatca gctttctaaa aaggaagctt ccagacacgc tatcatgcgt
 781 tctcctcaga tggtgtctgc tattgtacgt accatgcaga atacaaatga tgtagaaaca 841 gctcgttgta ccgctgggac cttgcataac ctttcccatc atcgtgaggg cttactggcc
        SEQ ID NO: 16                                             SEQ ID
  NO: 17
 901 atctttaagt ctggaggcat tcctgccctg gtgaaaatgc ttggttcacc agtggattct
                                                         SEQ ID NO: 18
 961 gtgttgtttt atgccattac aactctccac aaccttttat tacatcaaga aggagctaaa 1021 atggcagtgc gtttagctgg tgggctgcag aaaatggttg ccttgctcaa caaaacaaat
        SEQ ID NO: 33
1081 gttaaattct tggctattac gacagactgc cttcaaattt tagcttatgg caaccaagaa
1141 agcaagctca tcatactggc tagtggtgga ccccaagctt tagtaaatat aatgaggacc
                                                SEQ ID NO: 34
1201 tatacttacg aaaaactact gtggaccaca agcagagtgc tgaaggtgct atctgtctgc
                               SEQ ID NO: 49
1261 tctagtaata agccggctat tgtagaagct ggtggaatgc aagctttagg acttcacctg
                                  SEQ ID NO: 50
1321 acagatccaa gtcaacgtct tgttcagaac tgtctttgga ctctcaggaa tctttcagat
1381 gctgcaacta aacaggaagg gatgaaggt ctccttggga ctcttgttca gcttctgggt
1441 tcagatgata taaatgtggt cacctgtgca gctggaattc tttctaacct cacttgcaat
                                              SEQ ID NO: 51
1501 aattataaga acaagatgat ggtctgccaa gtgggtggta tagaggctct tgtgcgtact
1561 gtccttcggg ctggtgacag gaagacatc actgagcctg ccatctgtgc tcttcgtcat
1621 ctgaccagcc gacaccaaga agccagagtg gcccagaatg cagttcgcct tcactatgga
1681 ctaccagttg tggttaagct cttacaccca ccatcccact ggcctctgat aaaggctact
1741 gttggattga ttcgaaatct tgcccttttgt cccgcaaatc atgcaccttt gcgtgagcag
1801 ggtgccattc cacgactagt tcagttgctt gttcgtgcac atcaggatac ccagcgccgt
1861 acgtccatgg gtgggacaca gcagcaattt gtggaggggg tccgcatgga agaaatagtt
1921 gaaggttgta ccggagccct tcacatccta gctcgggatg ttcacaaccg aattgttatc
                    SEQ ID NO: 52
1981 agaggactaa ataccattcc attgtttgtg cagctgcttt attctcccat tgaaaacatc
        SEQ ID NO: 53
2041 caaagagtag ctgcaggggt cctctgtgaa cttgctcagg acaaggaagc tgcagaagct
                         SEQ ID NO: 54
2101 attgaagctg agggagccac agctcctctg acagagttac ttcactctag aatgaaggt
2161 gtggcgacat atgcagctgc tgttttgttc cgaatgtctg aggacaagcc acaagattac
                                                           SEQ ID NO: 55
2221 aagaaacggc tttcagttga gctgaccagc tctctcttca gaacagagcc aatggcttgg
2281 aatgagactg ctgatcttgg acttgatatt ggtgcccagg gagaaccct tggatatcgc
```

Figure 1 (cont'd)

SEQ ID NO: 56
```
2341 caggatgatc ctagctatcg ttctttcac tctggtggat atggccagga tgcctgggt
2401 atggacccca tgatggaaca tgagatgggt ggccaccacc ctgtgctga ctatccagtt
```
SEQ ID NO: 57
```
2461 gatgggctgc cagatctggg gcatgcccag gacctcatgg atgggctgcc tccaggtgac
2521 agcaatcagc tggcctggtt tgatactgac ctgtaaatca tcctttaggt aagaagtttt
2581 aaaaagccag tttgggtaaa atacttttac tctgcctaca gaacttcaga aagacttggt
2641 tggtagggtg ggagtggttt aggctatttg taaatctgcc acaaaaacag gtatatactt
2701 tgaaaggaga tgtcttggaa cattggaatg ttctcagatt tctggttgtt atgtgatcat
2761 gtgtggaagt tattaacttt aatgttttt gccacagctt ttgcaactta atactcaaat
2821 gagtaacatt tgctgtttta aacattaata gcagcctttc tctctttata cagctgtatt
2881 gtctgaactt gcattgtgat tggcctgtag agttgctgag agggctcgag gggtgggctg
2941 gtatctcaga aagtgcctga cacactaacc aagctgagtt tcctatggga acaattgaag
3001 taaactttt gttctggtcc ttttggtcg aggagtaaca atacaaatgg attttgggag
```
SEQ ID NO: 58
```
3061 tgactcaaga agtgaagaat gcacaagaat ggatcacaag atggaattta gcaaaccccta
3121 gccttgcttg ttaaaatttt tttttttttt ttttaagaat atctgtaatg gtactgactt
3181 tgcttgcttt gaagtagctc tttttttttt tttttttttt ttttttgc agtaactgtt
```
SEQ ID NO: 88
```
3241 ttttaagtct ctcgtagtgt taagttatag tgaatactgc tacagcaatt tctaatttt
```
SEQ ID NO: 103
```
3301 aagaattgag taatggtgta gaacactaat taattcataa tcactctaat taattgtaat
3361 ctgaataaag tgtaacaatt gtgtagcctt tttgtataaa atagacaaat agaaaatggt
```

SEQ ID NO: 118
```
3421 ccaattagtt tccttttaa tatgcttaaa ataagcaggt ggatctattt catgttttg
3481 atcaaaaact atttgggata tgtatgggta gggtaaatca gtaagaggtg ttatttggaa
3541 ccttgttttg gacagtttac cagttgcctt ttatcccaaa gttgttgtaa cctgctgtga
3601 tacgatgctt caagagaaaa tgcggttata aaaatggtt cagaattaaa cttttaattc
3661 attcaaaaaa aaaaaaaaaa aaaaaaaaaa aaaaaa
```

Figure 6:

```
   1 aggatacagc ggcttctgcg cgacttataa gagctccttg tgcggcgcca ttaagcct
  61 ctcggtctgt ggcagcagcg ttggcccggc cccgggagcg gagagcgagg ggaggcggag
 121 acggaggaag gtctgaggag cagcttcagt cccgccgag ccgccaccgc aggtcgagga
 181 cggtcggact cccgcggcgg gaggagcctg ttcccctgag ggtatttgaa gtataccata
 241 caactgtttt gaaaatccag cgtggacaat ggctactcaa gctgattga tggagttgga
 301 catggccatg gaaccagaca gaaaagcggc tgttagtcac tggcagcaac agtcttacct
 361 ggactctgga atccattctg gtgccactac cacagctcct tctctgagtg gtaaaggcaa
 421 tcctgaggaa gaggatgtgg atacctccca agtcctgtat gagtgggaac agggattttc
 481 tcagtccttc actcaagaac aagtagctga tattgatgga cagtatgcaa tgactcgagc
 541 tcagagggta cgagctgcta tgttccctga gacattagat gagggcatgc agatccatc
 601 tacacagttt gatgctgctc atcccactaa tgtccagcgt ttggctgaac catcacagat
 661 gctgaaacat gcagttgtaa actgattaa ctatcaagat gatgcagaac ttgccacacg
 721 tgcaatccct gaactgacaa aactgctaaa tgacgaggac caggtggtgg ttaataaggc
 781 tgcagttatg gtccatcagc tttctaaaaa ggaagcttcc agacacgcta tcatgcgttc
 841 tcctcagatg gtgtctgcta ttgtacgtac catgcagaat acaaatgatg tagaaacagc
 901 tcgttgtacc gctgggacct tgcataacct ttcccatcat cgtgagggct tactggccat
 961 cttaagtct ggaggcattc ctgccctggt gaaaatgctt ggttcaccag tggattctgt
1021 gttgtttat gccattacaa ctctccacaa cctttatta catcaagaag gagctaaaat
1081 ggcagtgcgt ttagctggtg ggctgcagaa aatggttgcc ttgctcaaca aaacaaatgt
1141 taaattcttg gctattacga cagactgcct tcaaatttta gcttatggca accaagaaag
1201 caagctcatc atactggcta gtggtggacc ccaagcttta gtaaatataa tgaggaccta
1261 tacttacgaa aaactactgt ggaccacaag cagagtgctg aaggtgctat ctgtctgctc
1321 tagtaataag ccggctattg tagaagctgg tggaatgcaa gctttaggac ttcacctgac
1381 agatccaagt caacgtcttg ttcagaactg tctttggact ctcaggaatc tttcagatgc
1441 tgcaactaaa caggaaggga tggaaggtct ccttgggact cttgttcagc ttctgggttc
1501 agatgatata aatgtggtca cctgtgcagc tggaattctt tctaacctca cttgcaataa
1561 ttataagaac aagatgatgg tctgccaagt gggtggtata gaggctcttg tgcgtactgt
1621 ccttcgggct ggtgacaggg aagacatcac tgagcctgcc atctgtgctc ttcgtcatct
1681 gaccagccga caccaagaag cagagatggc ccagaatgca gttcgccttc actatggact
1741 accagttgtg gttaagctct tacacccacc atcccactgg cctctgataa aggctactgt
1801 tggattgatt cgaaatcttg ccctttgtcc cgcaaatcat gcacctttgc gtgagcaggg
1861 tgccattcca cgactagttc agttgcttgt tcgtgcacat caggatacc agcgccgtac
1921 gtccatgggt gggacacagc agcaatttgt ggaggggtc cgcatggaag aaatagttga
1981 aggttgtacc ggagcccttc acatcctagc tcgggatgtt cacaaccgaa ttgttatcag
2041 aggactaaat accattccat tgttgtgca gctgctttat tctcccattg aaaacatcca
2101 aagagtagct gcaggggtcc tctgtgaact tgctcaggac aaggaagctg cagaagctat
2161 tgaagctgag ggagccacag ctcctctgac agagttactt cactctagga atgaaggtgt
2221 ggcgacatat gcagctgctg ttttgttccg aatgtctgag gacaagccac aagattacaa
2281 gaaacggctt tcagttgagc tgaccagctc tctcttcaga acagagccaa tggcttggaa
2341 tgagactgct gatcttggac ttgatattgg tgcccaggga gaaccccttg gatatcgcca
2401 ggatgatcct agctatcgtt ctttcactc tggtggatat ggccaggatg cctgggtat
2461 ggaccccatg atggaacatg agatgggtgg ccaccaccct ggtgctgact atccagttga
2521 tgggctgcca gatctggggc atgcccagga cctcatggat gggctgcctc caggtgacag
2581 caatcagctg gcctggtttaa atactgacct gtaaatcatc ctttaggtaa gaagtttaa
2641 aaagccagtt tggggtaaaat acttttactc tgcctacaga acttcagaaa gacttggttg
2701 gtagggtggg agtggtttag gctatttgta aatctgccac aaaaacaggt atatacttg
2761 aaaggagatg tcttggaaca ttgaatgtt ctcagattc tggttgttat gtgatcatgt
2821 gtggaagtta ttaactttaa tgtttttgc cacagctttt gcaacttaat actcaaatga
2881 gtaacatttg ctgttttaaa cattaatagc agcctttctc tctttataca gctgtattgt
```

Figure 6 (Cont'd)

```
2941 ctgaacttgc attgtgattg gcctgtagag ttgctgagag ggctcgaggg gtgggctggt
3001 atctcagaaa gtgcctgaca cactaaccaa gctgagtttc ctatgggaac aattgaagta
3061 aactttttgt tctggtcctt tttggtcgag gagtaacaat acaaatggat tttgggagtg
3121 actcaagaag tgaagaatgc acaagaatgg atcacaagat ggaatttatc aaaccctagc
3181 cttgcttgtt aaatttttt tttttttt ttaagaatat ctgtaatggt actgactttg
3241 cttgctttga agtagctctt ttttttttt tttttttt tttgcagtaa ctgttttta
3301 agtctctcgt agtgttaagt tatagtgaat actgctacag caatttctaa ttttaagaa
3361 ttgagtaatg gtgtagaaca ctaattcata atcactctaa ttaattgtaa tctgaataaa
3421 gtgtaacaat tgtgtagcct ttttgtataa aatagacaaa tagaaaatgg tccaattagt
3481 ttccttttta atatgcttaa aataagcagg tggatctatt tcatgttttt gatcaaaaac
3541 tatttgggat atgtatgggt agggtaaatc agtaagaggt gttatttgga accttgtttt
3601 ggacagttta ccagttgcct tttatcccaa agttgttgta acctgctgtg atacgatgct
3661 tcaagagaaa atgcggttat aaaaaatggt tcagaattaa acttttaatt cattcgattg
```

COMPOUNDS FOR THE MODULATION OF BETA-CATENIN EXPRESSION

1. CROSS-REFERENCE TO RELATED APPLICATIONS

This application claims the benefit under 35 U.S.C. §119 (e) of U.S. Provisional Application Ser. No. 60/915,371, filed May 1, 2007, and U.S. Provisional Application Ser. No. 61/023,244, filed Jan. 24, 2008, the disclosures of which are incorporated herein by reference in their entireties.

2. FIELD OF THE INVENTION

The invention relates to oligomeric compounds (oligomers) which target beta-catenin mRNA in a cell, leading to reduced expression of beta-catenin. Reduction of beta-catenin expression is beneficial for a range of medical disorders, such as hyperproliferative diseases, including cancer. The invention provides therapeutic compositions comprising oligomers and methods for modulating the expression of beta-catenin using said oligomers, including methods of treatment.

3. BACKGROUND

Beta-catenin (also known as cadherin-associated protein and β-Catenin) is a member of the catenin family of cytosolic proteins and a pivotal player in the signalling pathway initiated by Wnt proteins, mediators of several developmental processes. Beta-catenin undergoes phosphorylation upon growth factor stimulation resulting in reduced cell adhesion.

The role of beta-catenin in the development of cancer has been shown to be regulated by the expression product of the APC (adenomatous polyposis of the colon) gene. The APC tumor suppressor protein binds to beta-catenin, while beta-catenin was shown to interact with Tcf and Lef transcription factors. Morin et al. (Morin et al., Science, 1997, 275, 1787-1790) report that APC protein down-regulates the transcriptional activation mediated by beta-catenin and Tcf-4 in colon cancer. Their results indicate that the regulation of beta-catenin is critical to APC's tumor suppressive effect and that this regulation can be circumvented by mutations in either APC or beta-catenin.

Morin et al. showed that mutations of beta-catenin which affect phosphorylation sites rendered the cells insensitive to APC-mediated down-regulation of beta-atenin and that this disrupted mechanism was critical to colorectal tumorigenesis (Morin et al., Science, 1997, 275, 1787-1790).

Several studies report on the detection of mutations in beta-catenin in various cancer cell lines and abnormally high amounts of beta-catenin have been found in melanoma cell lines.

U.S. Pat. No. 6,066,500 to Bennett et al. describes antisense compounds, compositions and methods for modulating the expression of beta-catenin.

Considering the involvement of beta-catenin in the development of cancer, there remains a need for agents capable of effectively inhibiting beta-catenin function.

4. SUMMARY OF THE INVENTION

The invention provides an oligomer of 10-50 contiguous monomers wherein the sequence of said oligomer is at least 80% identical to the sequence of the reverse complement of a target region of a nucleic acid which encodes a mammalian beta-catenin.

The invention provides an oligomer of 10-50 contiguous monomers which comprises a first region, wherein the sequence of the first region is at least 80% identical to the sequence of the reverse complement of a target region of SEQ ID NO 173 or to a sequence selected from SEQ ID NOs: 1-132, SEQ ID NOs 174-192 and SEQ ID NO: 193.

The invention further provides a conjugate comprising the oligomer according to the invention, which, is covalently linked to one or more moieties that are not themselves nucleic acids or monomers ("conjugated moiety"). In some embodiments, the conjugated moiety consists of or comprises a sterol group such as cholesterol, or other moiety that facilitates entry into the cell.

The invention provides for a conjugate comprising the oligomer according to the invention, which is covalently linked to a polymeric conjugated moiety containing positively charged groups, such as polyethylene glycol (PEG)— i.e. the oligomer according to the invention may, optionally, be pegylated.

The invention provides for pharmaceutical compositions comprising the oligomer or conjugate of the invention, and a pharmaceutically acceptable diluent, carrier, salt or adjuvant.

The invention further provides for an oligomer or conjugate according to the invention, for use in medicine.

The invention further provides for the use of the oligomer or conjugate of the invention for the manufacture of a medicament for the treatment of one or more of the diseases referred to herein, such as a hyperproliferative disease, e.g., cancer.

The invention further provides for an oligomer or conjugate according to the invention, for use for the treatment of one or more of the diseases referred to herein, such as cancer.

Pharmaceutical and other compositions comprising the oligomer or conjugate of the invention are also provided. Further provided are methods of down-regulating the expression of beta-catenin in cells or tissues comprising contacting said cells or tissues, in vitro or in vivo, with an effective amount of one or more of the oligomers, conjugates or compositions of the invention.

Also disclosed are methods of treating an animal or a human, suspected of having or being prone to a disease or condition associated with expression or over-expression of beta-catenin, by administering to said animal or human a therapeutically or prophylactically effective amount of one or more of the oligomers, conjugates or compositions of the invention.

Further, methods of using oligomers for the inhibition of expression of beta-catenin, and for treatment of diseases associated with activity of beta-catenin are provided.

The invention provides for a method of inhibiting or reducing the expression of beta-catenin in a cell or a tissue, the method comprising the step of contacting said cell or tissue with an effective amount of an oligomer, a conjugate, or a pharmaceutical composition according to the invention so that expression of beta-catenin is inhibited or reduced.

The invention provides for a method of triggering apoptosis in a cell, such as a cancer cell, said method comprising the step of contacting said cell or tissue with an effective amount of an oligomer, a conjugate, or a pharmaceutical composition according to the invention so that either expression of beta-catenin is inhibited or reduced and/or apoptosis is triggered.

The invention further provides for an oligomer which comprises or consists of contiguous covalently linked monomers, wherein the oligomer comprises a first region, wherein the sequence of said first region is at least 80% identical to the sequence of a region of SEQ ID NOs 1-132 or SEQ ID NOs 174-193. In some embodiments, the sequence is selected from the group consisting of SEQ ID NO 189, 192, 58 and 103.

The invention further provides for an oligomer which comprises or consists of a first region, wherein the sequence of said first region is identical to the sequence of a region of SEQ ID NO 174-193, such as a region of SEQ ID NO 189 or 192.

The invention further provides for an oligomer which comprises or consists of a sequence identically present in SEQ ID NO 133-174, such as identically present in SEQ ID NO 168 or 171.

5. BRIEF DESCRIPTION OF THE FIGURES

FIG. 1: The beta-catenin sequences that are targeted by the oligomers having the sequence of SEQ ID NOs: 1, 16, 17, 18, 33, 34, 49, 50, 51, 52, 53, 54, 55, 56, 57, 58, 73, 88, 103 and 118, respectively, are shown in bold and underlined, indicating their position in the beta-catenin transcript (GenBank Accession number NM_001904—SEQ ID NO: 173).

FIG. 2: Beta-catenin expression normalized to GAPDH 24 hours after transfection of SW480 cells.

Figure 3:
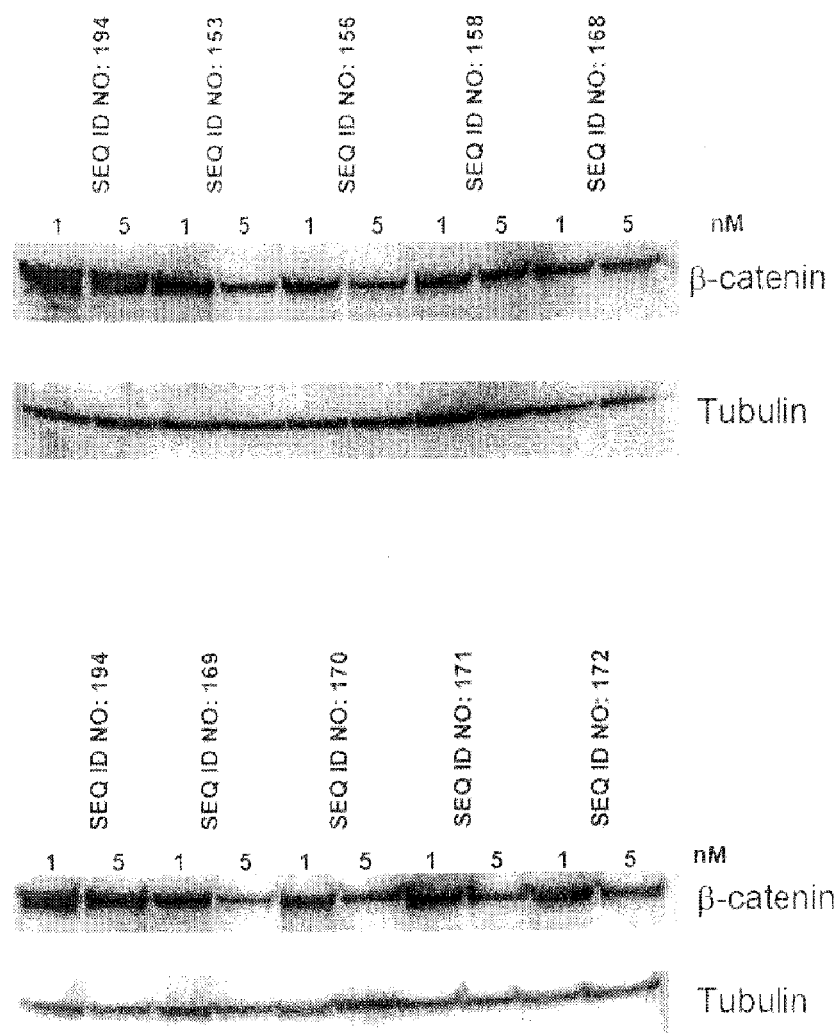

FIG. 3: Beta-catenin protein content in SW480 cells transfected with oligonucleotides at 1 and 5 nM concentration measured by Western blot. Tubulin staining was used as loading control and SEQ ID NO: 194 was used as a scrambled control oligonucleotide.

Figure 4:
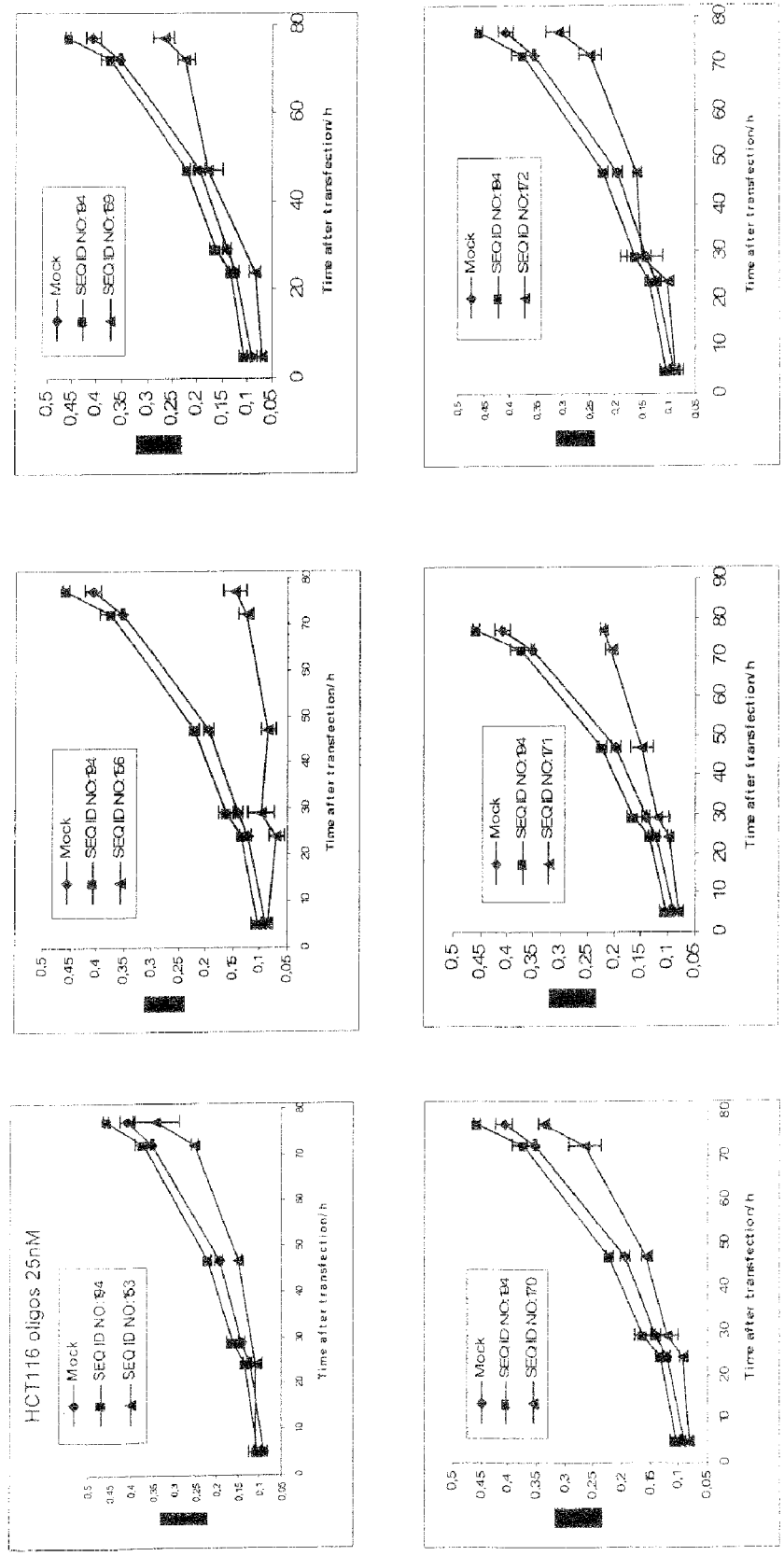

FIG. 4: Cellular proliferation measured using MTS assay in HCT116 cells transfected with oligonucleotides at 25 nM concentration measured as OD490 at different timepoints after transfection. Mock transfected cells and cells transfected with SEQ ID NO: 194 (scrambled control) were used as controls.

Figure 5:
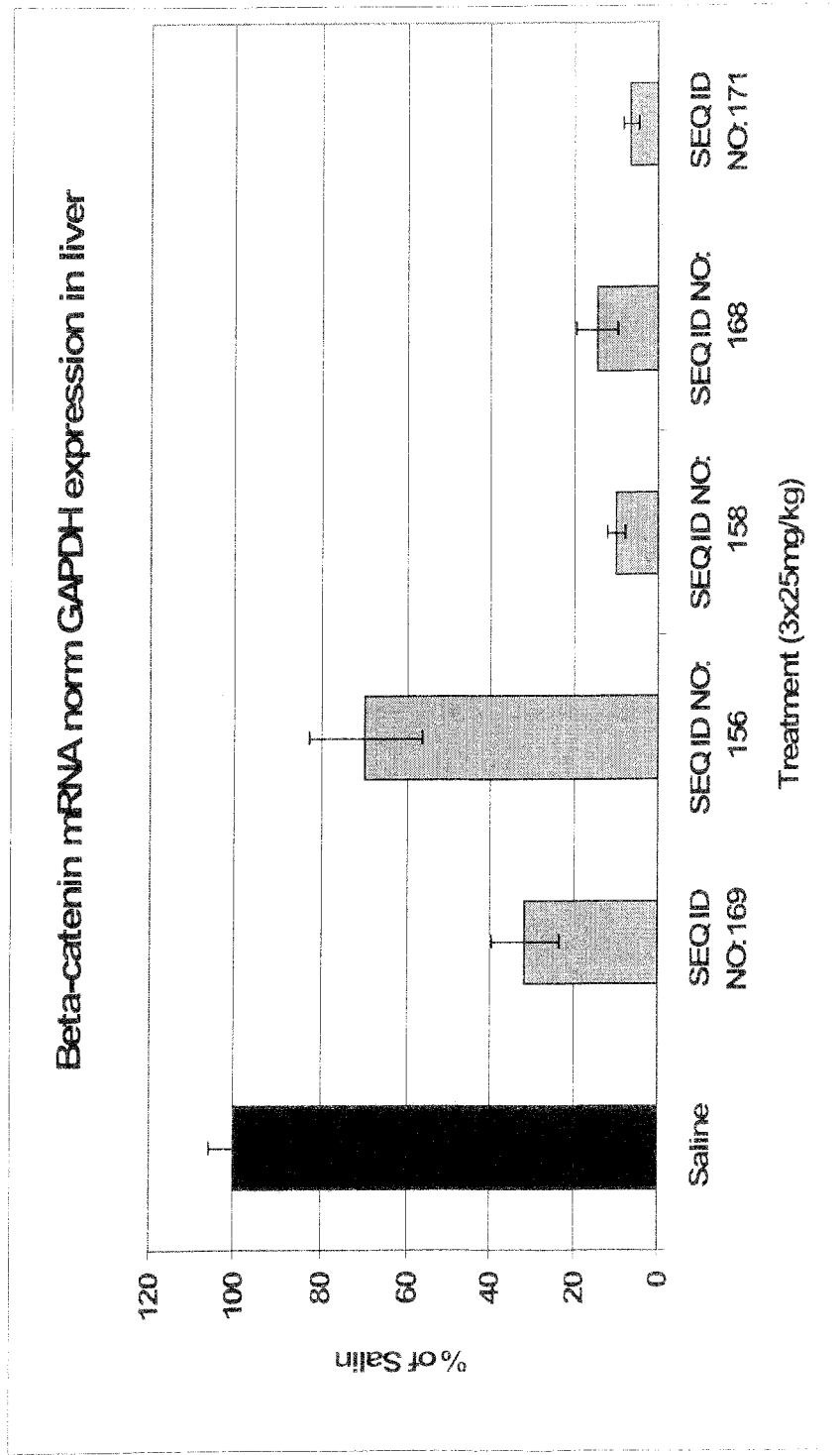

FIG. 5: Beta-catenin mRNA expression relative to saline treated control in mouse liver measured by QPCR after treatment with 3×25 mg/kg oligonucleotide i.v. Beta-catenin expression was normalized to GAPDH and results were plotted relative to saline treated control.

FIG. 6: The nucleotide sequence of a human beta-catenin mRNA having Accession No: NM_001904.3 (SEQ ID NO: 195).

6. DETAILED DESCRIPTION

The Oligomer

In a first aspect, oligomeric compounds (referred herein as oligomers) are provided that are useful, e.g., in modulating the function of nucleic acid molecules encoding mammalian beta-catenin, such as the beta-catenin nucleic acid shown in SEQ ID NO: 173, and naturally occurring allelic variants of such nucleic acid molecules encoding mammalian beta-catenin. The oligomers of the invention are composed of covalently linked monomers.

The term "monomer" includes both nucleosides and deoxynucleosides (collectively, "nucleosides") that occur naturally in nucleic acids and that do not contain either modified sugars or modified nucleobases, i.e., compounds in which a ribose sugar or deoxyribose sugar is covalently bonded to a naturally-occurring, unmodified, nucleobase (base) moiety (i.e., the purine and pyrimidine heterocycles adenine, guanine, cytosine, thymine or uracil) and "nucleoside analogues", which are nucleosides that either do occur naturally in nucleic acids or do not occur naturally in nucleic acids, wherein either the sugar moiety is other than a ribose or a deoxyribose sugar (such as bicyclic sugars or 2' modified sugars, such as 2' substituted sugars), or the base moiety is modified (e.g., 5-methylcytosine), or both.

An "RNA monomer" is a nucleoside containing a ribose sugar and an unmodified nucleobase.

A "DNA monomer" is a nucleoside containing a deoxyribose sugar and an unmodified nucleobase.

A "Locked Nucleic Acid monomer", "locked monomer", or "LNA monomer" is a nucleoside analogue having a bicyclic sugar, as further described herein below.

The terms "corresponding nucleoside analogue" and "corresponding nucleoside" indicate that the base moiety in the nucleoside analogue and the base moiety in the nucleoside are identical. For example, when the "nucleoside" contains a 2-deoxyribose sugar linked to an adenine, the "corresponding nucleoside analogue" contains, for example, a modified sugar linked to an adenine base moiety.

The terms "oligomer", "oligomeric compound", and "oligonucleotide" are used interchangeably in the context of the invention, and refer to a molecule formed by covalent linkage of two or more contiguous monomers by, for example, a phosphate group (forming a phosphodiester linkage between nucleosides) or a phosphorothioate group (forming a phosphothioester linkage between nucleosides). The oligomer consists of, or comprises, 10-50 monomers.

In some embodiments, an oligomer comprises nucleosides, or nucleoside analogues, or mixtures thereof as referred to herein. An "LNA oligomer" or "LNA oligonucleotide" refers to an oligonucleotide containing one or more LNA monomers.

Nucleoside analogues that are optionally included within oligomers may function similarly to corresponding nucleosides, or may have specific improved functions. Oligomers wherein some or all of the monomers are nucleoside analogues are often preferred over native forms because of several desirable properties of such oligomers, such as the ability to penetrate a cell membrane, good resistance to extra- and/or intracellular nucleases, and high affinity and specificity for the nucleic acid target. LNA monomers are particularly preferred, for example, for conferring several of the above-mentioned properties.

In various embodiments, one or more nucleoside analogues present within the oligomer are "silent" or "equivalent" in function to the corresponding natural nucleoside, i.e. have no functional effect on the way the oligomer functions to inhibit target gene expression. Such "equivalent" nucleoside analogues are nevertheless useful if, for example, they are easier or cheaper to manufacture, or are more stable under storage or manufacturing conditions, or can incorporate a tag or label. Typically, however, the analogues will have a functional effect on the way in which the oligomer functions to inhibit expression; for example by producing increased binding affinity to the target region of the target nucleic acid and/or increased resistance to intracellular nucleases and/or increased ease of transport into the cell.

Thus, in various embodiments, oligomers according to the invention comprise both nucleoside monomers and at least one nucleoside analogue monomer, such as an LNA monomer, or other nucleoside analogue monomers.

The term "at least one" comprises the integers larger than or equal to 1, such as 1, 2, 3, 4, 5, 6, 7, 8, 9, 10, 11, 12, 13, 14, 15, 16, 17, 18, 19, 20 and so forth. In various embodiments, such as when referring to the nucleic acid or protein targets of the compounds of the invention, the term "at least one" includes the terms "at least two" and "at least three" and "at least four", likewise the term "at least two" may comprise the terms at "least three" and "at least four".

In various embodiments, the oligomer consists of 10-50 monomers, preferably 10-25 monomers, more preferably 10-16 monomers, and even more preferably 12-16 monomers.

In various embodiments, the oligomer of the invention does not comprise RNA monomers.

The term "region", when used to refer to the oligomers of the invention, means a number of contiguous monomers within the oligomer, wherein the number of monomers in the "region" is less than the total number of monomers in the oligomer.

It is preferred that the oligomers according to the invention are linear molecules, or are linear as synthesised. The oligomer is, in such embodiments, a single stranded molecule, and typically does not comprise a short region of, for example, at least 3, 4 or 5 contiguous monomers, which are complementary to another region within the same oligomer such that the oligomer forms an internal duplex. In various embodiments, the oligomer is not substantially double-stranded, i.e., is not a siRNA.

In some embodiments, the oligomer of the invention consists of a contiguous stretch of monomers, the sequence of which is identified by a SEQ ID No. disclosed herein (see, e.g., Tables 1-4). In other embodiments, the oligomer comprises a first region, the region consisting of a contiguous stretch of monomers, and one or more additional regions which consist of at least one additional monomer. In some embodiments, the sequence of the first region is identified by a SEQ ID No. disclosed herein.

Target Nucleic Acid

The terms "nucleic acid" and "polynucleotide" are used interchangeably herein, and are defined as a molecule formed by covalent linkage of two or more monomers, as above-described. Including 2 or more monomers, "nucleic acids" may be of any length, and the term is generic to "oligomers", which have the lengths described herein. The terms "nucleic acid" and "polynucleotide" include single-stranded, double-stranded, partially double-stranded, and circular molecules.

The term "target nucleic acid", as used herein, refers to the nucleic acid (such as DNA) encoding mammalian beta-catenin polypeptide, such as human beta-catenin protein (e.g., such as the human gene exons having Accession Nos. X89579, X89593, X89592, X89591, X89588, X89585, X89584 and X89578), or a mammalian beta-catenin mRNA such as SEQ ID NO 173. Examples of other mammalian beta-catenin mRNAs include, but are not limited to, those having Accession Numbers NM_001098209, NM_0010987210 (human beta-catenin mRNA); NM_007614 (mouse beta-catenin mRNA); NM_053357 (rat beta-catenin mRNA); NM-001122762, DQ267491 (horse beta-catenin mRNA); NM_214367 (pig beta-catenin mRNA); BC119949, BT030683 (cow beta-catenin mRNA). "Target nucleic acid" also includes beta-catenin encoding nucleic acids or naturally occurring variants thereof, and RNA nucleic acids derived therefrom, preferably mRNA, such as pre-mRNA, although preferably mature mRNA. In various embodiments, for example when used in research or diagnostics, the "target nucleic acid" may be a cDNA or a synthetic oligonucleotide derived from the above DNA or RNA nucleic acid targets. The oligomers according to the invention are preferably capable of hybridising to the target nucleic acid.

The term "naturally occurring variant thereof" refers to variants of the beta-catenin polypeptide or nucleic acid sequence which exist naturally within the defined taxonomic group, such as mammalian, such as mouse, monkey, and preferably human. Typically, when referring to "naturally occurring variants" of a polynucleotide the term also may encompass any allelic variant of the beta-catenin-encoding genomic DNA which is found at the Chromosome Chr 3: 41.22-41.26 Mb by chromosomal translocation or duplication, and the RNA, such as mRNA derived therefrom. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

An oligomer of the invention binds to a region of the target nucleic acid (the "target region") by either Watson-Crick base pairing, Hoogsteen hydrogen bonding, or reversed Hoogsteen hydrogen bonding, between the monomers of the oligomer and monomers of the target nucleic acid. Unless otherwise indicated, binding is by Watson-Crick pairing of complementary bases, and the oligomer binds to the target because the sequence of the oligomer is identical to, or partially-identical to, the sequence of the reverse complement of the target region; for purposes herein, the oligomer is said to be "complementary" or "partially complementary" to the target region, and the percentage of "complementarity" of the oligomer sequence to that of the target region is the percentage "identity" to the reverse complement of the sequence of the target region.

Unless otherwise made clear by context, the "target region" herein will be the region of the target having the sequence that best aligns with the reverse complement of the sequence of the specified oligomer (or region thereof), using the alignment program and parameters described herein below.

In determining the degree of "complementarity" between oligomers of the invention (or regions thereof) and the target region of the nucleic acid which encodes mammalian beta-catenin, such as those disclosed herein, the degree of "complementarity" (also, "homology") is expressed as the percentage identity between the sequence of the oligomer (or region thereof) and the reverse complement of the sequence of the target region that best aligns therewith. The percentage is calculated by counting the number of aligned bases that are identical as between the 2 sequences, dividing by the total number of contiguous monomers in the oligomer, and multiplying by 100. In such a comparison, if gaps exist, it is preferable that such gaps are merely mismatches rather than areas where the number of monomers within the gap differ between the oligomer of the invention and the target region.

Amino acid and polynucleotide alignments, percentage sequence identity, and degree of complementarity may be determined for purposes of the invention using the ClustalW algorithm using standard settings: see http://www.ebi.ac.uk/emboss/align/index.html, Method: EMBOSS::water (local): Gap Open=10.0, Gap extend=0.5, using Blosum 62 (protein), or DNA full for nucleotide/nucleobase sequences.

As will be understood, depending on context, "mismatch" refers to a nonidentity in sequence (as, for example, between the nucleobase sequence of an oligomer and the reverse complement of the target region to which it binds; as for example, between the base sequence of two aligned beta-catenin encoding nucleic acids), or to noncomplementarity in sequence (as, for example, between an oligomer and the target region to which binds).

Suitably, the oligomer (or conjugate, as further described, below) is capable of inhibiting (such as, by down-regulating) expression of the beta-catenin gene.

In various embodiments, the oligomers of the invention effect inhibition of beta-catenin mRNA expression of at least 10% as compared to the normal expression level, at least 20%, more preferably at least 30%, 40%, 50%, 60%, 70%, 80%, 90% or 95% as compared to the normal expression level. In various embodiments, the oligomers of the invention effect inhibition of beta-catenin protein expression of at least 10% as compared to the normal expression level, at least 20%, more preferably at least 300%, 40%, 50%, 60%, 70%, 80%, 90% or 95% as compared to the normal expression level. In some embodiments, such inhibition is seen when using 1 nM of the oligomer or conjugate of the invention. In various embodiments, such inhibition is seen when using 25 nM of the oligomer or conjugate.

In various embodiments, the inhibition of mRNA expression is less than 100% (i.e., less than complete inhibition of expression), such as less than 98%, inhibition, less than 95% inhibition, less than 90% inhibition, less than 80% inhibition, such as less than 70% inhibition. In various embodiments, the inhibition of protein expression is less than 100% (i.e., less than complete inhibition of expression), such as less than 98%, inhibition, less than 95% inhibition, less than 90% inhibition, less than 80% inhibition, such as less than 70% inhibition.

Modulation (i.e., inhibition or increase) of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of inhibition when using an appropriate dosage, such as 1 and 25 nM, is, in various embodiments, typically to a level of 10-20% of the normal levels in the absence of the compound of the invention.

The invention therefore provides a method of inhibiting (e.g., by down-regulating) the expression of beta-catenin protein and/or mRNA in a cell which is expressing beta-catenin protein and/or mRNA, the method comprising contacting the cell with an amount of the oligomer or conjugate according to the invention effective to inhibit (e.g., to down-regulate) the expression of beta-catenin protein and/or mRNA in said cell. Suitably the cell is a mammalian cell, such as a human cell. The contacting may occur, in certain embodiments, in vitro. In other embodiments, the contacting may be effected in vivo, by administering the compound or conjugate of the invention to a mammal.

An oligomer of the invention typically binds to a target region of the human beta-catenin mRNA, and as such, comprises or consists of a region having a base sequence that is complementary or partially complementary to the base sequence of, e.g., a target region of SEQ ID NO:173. The sequence of the oligomers of the invention may optionally comprise 1, 2, 3, 4 or more base mismatches when compared to the sequence of the best-aligned target region of SEQ ID NO: 173.

In some embodiments, the oligomers of the invention have sequences that are identical to a sequence selected from the group consisting of SEQ ID NOS: 1-132, shown in Table 1, below. In other embodiments, the oligomers of the invention have sequences that differ in one, two or three bases when compared to a sequence selected from the group consisting of SEQ ID NOs: 1-132. In some embodiments, the oligomers consist of or comprise 10-16 contiguous monomers. Examples of oligomers consisting of 16 contiguous monomers are SEQ ID NOS: 1, 16, 17, 18, 33, 34, 49, 50, 51, 52, 53, 54, 55, 56, 57, 58, 73, 88, 103, and 118. Shorter sequences can be derived therefrom, e.g., the sequence of the shorter oligomer may be identically present in a region of SEQ ID NOs: 1-132. Longer oligomers may include a region having a sequence of at least 10 contiguous monomers that is identically present in SEQ ID NOs: 1-132.

TABLE 1

Antisense oligonucleotide sequences (Motifs)

| SEQ ID NO | Sequence (5'-3') | Length (bases) | Description |
| --- | --- | --- | --- |
| SEQ ID NO: 1 | GAAAGCTGATGGACCA | 16 | Antisense oligo sequence |
| SEQ ID NO: 2 | GAAAGCTGATGGACC | 15 | as above |
| SEQ ID NO: 3 | AAAGCTGATGGACCA | 15 | as above |
| SEQ ID NO: 4 | GAAAGCTGATGGAC | 14 | as above |
| SEQ ID NO: 5 | AAAGCTGATGGACC | 14 | as above |
| SEQ ID NO: 6 | AAGCTGATGGACCA | 14 | as above |
| SEQ ID NO: 7 | GAAAGCTGATGGA | 13 | as above |
| SEQ ID NO: 8 | AAAGCTGATGGAC | 13 | as above |
| SEQ ID NO: 9 | AAGCTGATGGACC | 13 | as above |
| SEQ ID NO: 10 | AGCTGATGGACCA | 13 | as above |
| SEQ ID NO: 11 | GAAAGCTGATGG | 12 | as above |
| SEQ ID NO: 12 | AAAGCTGATGGA | 12 | as above |
| SEQ ID NO: 13 | AAGCTGATGGAC | 12 | as above |
| SEQ ID NO: 14 | AGCTGATGGACC | 12 | as above |
| SEQ ID NO: 15 | GCTGATGGACCA | 12 | as above |
| SEQ ID NO: 16 | CAGACTTAAAGATGGC | 16 | as above |
| SEQ ID NO: 17 | CAGAATCCACTGGTGA | 16 | as above |
| SEQ ID NO: 18 | GCACTGCCATTTTAGC | 16 | as above |
| SEQ ID NO: 19 | GCACTGCCATTTTAG | 15 | as above |
| SEQ ID NO: 20 | CACTGCCATTTTAGC | 15 | as above |
| SEQ ID NO: 21 | GCACTGCCATTTTA | 14 | as above |
| SEQ ID NO: 22 | CACTGCCATTTTAG | 14 | as above |
| SEQ ID NO: 23 | ACTGCCATTTTAGC | 14 | as above |
| SEQ ID NO: 24 | GCACTGCCATTTT | 13 | as above |
| SEQ ID NO: 25 | CACTGCCATTTTA | 13 | as above |
| SEQ ID NO: 26 | ACTGCCATTTTAG | 13 | as above |
| SEQ ID NO: 27 | CTGCCATTTTAGC | 13 | as above |
| SEQ ID NO: 28 | GCACTGCCATTT | 12 | as above |
| SEQ ID NO: 29 | CACTGCCATTTT | 12 | as above |
| SEQ ID NO: 30 | ACTGCCATTTTA | 12 | as above |
| SEQ ID NO: 31 | CTGCCATTTTAG | 12 | as above |
| SEQ ID NO: 32 | TGCCATTTTAGC | 12 | as above |
| SEQ ID NO: 33 | GTAATAGCCAAGAATT | 16 | as above |
| SEQ ID NO: 34 | ACTCTGCTTGTGGTCC | 16 | as above |
| SEQ ID NO: 35 | ACTCTGCTTGTGGTC | 15 | as above |

TABLE 1-continued

Antisense oligonucleotide sequences (Motifs)

| SEQ ID NO | Sequence (5'-3') | Length (bases) | Description |
|---|---|---|---|
| SEQ ID NO: 36 | CTCTGCTTGTGGTCC | 15 | as above |
| SEQ ID NO: 37 | ACTCTGCTTGTGGT | 14 | as above |
| SEQ ID NO: 38 | CTCTGCTTGTGGTC | 14 | as above |
| SEQ ID NO: 39 | TCTGCTTGTGGTCC | 14 | as above |
| SEQ ID NO: 40 | ACTCTGCTTGTGG | 13 | as above |
| SEQ ID NO: 41 | CTCTGCTTGTGGT | 13 | as above |
| SEQ ID NO: 42 | TCTGCTTGTGGTC | 13 | as above |
| SEQ ID NO: 43 | CTGCTTGTGGTCC | 13 | as above |
| SEQ ID NO: 44 | ACTCTGCTTGTG | 12 | as above |
| SEQ ID NO: 45 | CTCTGCTTGTGG | 12 | as above |
| SEQ ID NO: 46 | TCTGCTTGTGGT | 12 | as above |
| SEQ ID NO: 47 | CTGCTTGTGGTC | 12 | as above |
| SEQ ID NO: 48 | TGCTTGTGGTCC | 12 | as above |
| SEQ ID NO: 49 | CCACCAGCTTCTACAA | 16 | as above |
| SEQ ID NO: 50 | GAGTCCAAAGACAGTT | 16 | as above |
| SEQ ID NO: 51 | ACCCACTTGGCAGACC | 16 | as above |
| SEQ ID NO: 52 | GCACAAACAATGGAAT | 16 | as above |
| SEQ ID NO: 53 | GCAGCTACTCTTTGGA | 16 | as above |
| SEQ ID NO: 54 | CTCCCTCAGCTTCAAT | 16 | as above |
| SEQ ID NO: 55 | GCAGTCTCATTCCAAG | 16 | as above |
| SEQ ID NO: 56 | TATCCACCAGAGTGAA | 16 | as above |
| SEQ ID NO: 57 | CATCCATGAGGTCCTG | 16 | as above |
| SEQ ID NO: 58 | CCATCTTGTGATCCAT | 16 | as above |
| SEQ ID NO: 59 | CCATCTTGTGATCCA | 15 | as above |
| SEQ ID NO: 60 | CATCTTGTGATCCAT | 15 | as above |
| SEQ ID NO: 61 | CCATCTTGTGATCC | 14 | as above |
| SEQ ID NO: 62 | CATCTTGTGATCCA | 14 | as above |
| SEQ ID NO: 63 | ATCTTGTGATCCAT | 14 | as above |
| SEQ ID NO: 64 | CCATCTTGTGATC | 13 | as above |
| SEQ ID NO: 65 | CATCTTGTGATCC | 13 | as above |
| SEQ ID NO: 66 | ATCTTGTGATCCA | 13 | as above |
| SEQ ID NO: 67 | TCTTGTGATCCAT | 13 | as above |
| SEQ ID NO: 68 | CCATCTTGTGAT | 12 | as above |
| SEQ ID NO: 69 | CATCTTGTGATC | 12 | as above |
| SEQ ID NO: 70 | ATCTTGTGATCC | 12 | as above |
| SEQ ID NO: 71 | TCTTGTGATCCA | 12 | as above |
| SEQ ID NO: 72 | CTTGTGATCCAT | 12 | as above |
| SEQ ID NO: 73 | AAGCAAGCAAAGTCAG | 16 | as above |
| SEQ ID NO: 74 | AAGCAAGCAAAGTCA | 15 | as above |
| SEQ ID NO: 75 | AGCAAGCAAAGTCAG | 15 | as above |
| SEQ ID NO: 76 | AAGCAAGCAAAGTC | 14 | as above |
| SEQ ID NO: 77 | AGCAAGCAAAGTC | 13 | as above |
| SEQ ID NO: 78 | GCAAGCAAAGTCAG | 14 | as above |
| SEQ ID NO: 79 | AAGCAAGCAAAGT | 13 | as above |
| SEQ ID NO: 80 | AGCAAGCAAAGTC | 13 | as above |
| SEQ ID NO: 81 | GCAAGCAAAGTCA | 13 | as above |
| SEQ ID NO: 82 | CAAGCAAAGTCAG | 13 | as above |
| SEQ ID NO: 83 | AAGCAAGCAAAG | 12 | as above |
| SEQ ID NO: 84 | AGCAAGCAAAGT | 12 | as above |
| SEQ ID NO: 85 | GCAAGCAAAGTC | 12 | as above |
| SEQ ID NO: 86 | CAAGCAAAGTCA | 12 | as above |
| SEQ ID NO: 87 | AAGCAAAGTCAG | 12 | as above |
| SEQ ID NO: 88 | GAAATTGCTGTAGCAG | 16 | as above |
| SEQ ID NO: 89 | GAAATTGCTGTAGCA | 15 | as above |
| SEQ ID NO: 90 | AAATTGCTGTAGCAG | 15 | as above |
| SEQ ID NO: 91 | GAAATTGCTGTAGC | 14 | as above |
| SEQ ID NO: 92 | AAATTGCTGTAGCA | 14 | as above |
| SEQ ID NO: 93 | AATTGCTGTAGCAG | 14 | as above |
| SEQ ID NO: 94 | GAAATTGCTGTAG | 13 | as above |
| SEQ ID NO: 95 | AAATTGCTGTAGC | 13 | as above |
| SEQ ID NO: 96 | AATTGCTGTAGCA | 13 | as above |
| SEQ ID NO: 97 | ATTGCTGTAGCAG | 13 | as above |
| SEQ ID NO: 98 | GAAATTGCTGTA | 12 | as above |
| SEQ ID NO: 99 | AAATTGCTGTAG | 12 | as above |
| SEQ ID NO: 100 | AATTGCTGTAGC | 12 | as above |
| SEQ ID NO: 101 | ATTGCTGTAGCA | 12 | as above |
| SEQ ID NO: 102 | TTGCTGTAGCAG | 12 | as above |
| SEQ ID NO: 103 | GTGTTCTACACCATTA | 16 | as above |
| SEQ ID NO: 104 | GTGTTCTACACCATT | 15 | as above |
| SEQ ID NO: 105 | TGTTCTACACCATTA | 15 | as above |
| SEQ ID NO: 106 | GTGTTCTACACCAT | 14 | as above |
| SEQ ID NO: 107 | TGTTCTACACCATT | 14 | as above |
| SEQ ID NO: 108 | GTTCTACACCATTA | 14 | as above |
| SEQ ID NO: 109 | GTGTTCTACACCA | 13 | as above |
| SEQ ID NO: 110 | TGTTCTACACCAT | 13 | as above |
| SEQ ID NO: 111 | GTTCTACACCATT | 13 | as above |

TABLE 1-continued

Antisense oligonucleotide sequences (Motifs)

| SEQ ID NO | Sequence (5'-3') | Length (bases) | Description |
|---|---|---|---|
| SEQ ID NO: 112 | TTCTACACCATTA | 13 | as above |
| SEQ ID NO: 113 | GTGTTCTACACC | 12 | as above |
| SEQ ID NO: 114 | TGTTCTACACCA | 12 | as above |
| SEQ ID NO: 115 | GTTCTACACCAT | 12 | as above |
| SEQ ID NO: 116 | TTCTACACCATT | 12 | as above |
| SEQ ID NO: 117 | TCTACACCATTA | 12 | as above |
| SEQ ID NO: 118 | AACATGAAATAGATCC | 16 | as above |
| SEQ ID NO: 119 | AACATGAAATAGATC | 15 | as above |
| SEQ ID NO: 120 | ACATGAAATAGATCC | 15 | as above |
| SEQ ID NO: 121 | AACATGAAATAGAT | 14 | as above |
| SEQ ID NO: 122 | ACATGAAATAGATC | 14 | as above |
| SEQ ID NO: 123 | CATGAAATAGATCC | 14 | as above |
| SEQ ID NO: 124 | AACATGAAATAGA | 13 | as above |
| SEQ ID NO: 125 | ACATGAAATAGAT | 13 | as above |
| SEQ ID NO: 126 | CATGAAATAGATC | 13 | as above |
| SEQ ID NO: 127 | ATGAAATAGATCC | 13 | as above |
| SEQ ID NO: 128 | AACATGAAATAG | 12 | as above |
| SEQ ID NO: 129 | ACATGAAATAGA | 12 | as above |
| SEQ ID NO: 130 | CATGAAATAGAT | 12 | as above |
| SEQ ID NO: 131 | ATGAAATAGATC | 12 | as above |
| SEQ ID NO: 132 | TGAAATAGATCC | 12 | as above |

Further provided are target nucleic acids (i.e., DNA or mRNA encoding beta-catenin), that contain target regions that are complementary or partially-complementary to one or more of the oligomers of SEQ ID NOs 1-132, wherein said oligomers are capable of inhibiting expression (e.g., by down-regulation) of beta-catenin protein or mRNA. For example, target regions of human beta-catenin mRNA which are complementary to the antisense oligomers having the sequences of SEQ ID NOs: 1, 16, 17, 18, 33, 34, 49, 50, 51, 52, 53, 54, 55, 56, 57, 58, 73, 88, 103 and 118, are shown in FIG. 1 (bold and underlined, with the corresponding oligomer SEQ ID NOs indicated above).

The oligomer of the invention may, suitably, comprise a region having a particular sequence, such as an oligomer selected from SEQ ID NOS: 174-193, that is identically present in a shorter oligomer of the invention. Preferably, the region comprises 10-16 monomers. For example, SEQ ID NOs: 174-193 each comprise a region wherein the sequence of the region is identically present in the shorter oligomers having SEQ ID NOS: 1, 16, 17, 18, 33, 34, 49, 50, 51, 52, 53, 54, 55, 56, 57, 58, 73, 88, 103, and 118, respectively. In some embodiments, oligomers which have fewer than 16 monomers, such as 10, 11, 12, 13, 14, or 15, have a region of at least 8, at least 9, at least 10, at least 11, at least 12, at least 13, at least 14 or 15, contiguous monomers wherein the sequence of the region is identically present in SEQ ID NOS: 1, 16, 17, 18, 33, 34, 49, 50, 51, 52, 53, 54, 55, 56, 57, 58, 73, 88, 103, or 118. Hence, in various embodiments, shorter oligomers are derived from longer oligomers. In some embodiments, longer oligomers include all, or at least 10 contiguous monomers, from those exemplified SEQ ID NOs. Typically, if an oligomer of the invention comprises a first region having a sequence that is identically present in SEQ ID NOS: 1, 16, 17, 18, 33, 34, 49, 50, 51, 52, 53, 54, 55, 56, 57, 58, 73, 88, 103, or 118, and the oligomer is longer than the first region, then the other regions of the oligomer preferably flank the first region that is identically present in SEQ ID NOS: 1, 16, 17, 18, 33, 34, 49, 50, 51, 52, 53, 54, 55, 56, 57, 58, 73, 88, 103, or 118, the flanking regions of the oligomer having sequences that are complementary to the sequences flanking the target region of the target nucleic acid. Two such oligomers are SEQ ID NO 58 and SEQ ID NO 103.

Specific designs of oligomers of the invention are also disclosed, for example those shown in SEQ ID NOS: 133-152, in particular SEQ ID NOs: 133, 134, 135, 136, 138, 141, 148, 149, 150, 151 and 152. Specific designs of LNA oligonucleotides are also disclosed, for example those shown in SEQ ID NOS: 153-172, in particular SEQ ID NOS: 153, 154, 155, 156, 158, 161, 168, 169, 170, 171 and 172. The oligomers of the invention are, in preferred embodiments, potent inhibitors of beta-catenin mRNA and protein expression.

In various embodiments, the oligomer comprises or consists of a sequence of monomers which is fully complementary (perfectly complementary) to a target region of a target nucleic acid which encodes a mammalian beta-catenin. However, in some embodiments, the sequence of the oligomer includes 1, 2, 3, or 4 (or more) mismatches, as compared to the best-aligned target region, and still sufficiently binds to the target region to effect inhibition of beta-catenin mRNA or protein expression. The destabilizing effect of mismatches on the Watson-Crick hydrogen-bonded duplex may, for example, be compensated by increased length of the oligomer and/or an increased number of nucleoside analogues, such as LNA monomers, present within the oligomer.

In various embodiments, the oligomer base sequence comprises no more than 3, such as no more than 2, mismatches compared to the base sequence of the best-aligned target region of, for example, a nucleic acid which encodes a mammalian beta-catenin. In various embodiments, the oligomer base sequence comprises no more than a single mismatch compared to the base sequence of the best-aligned target region of, for example, a nucleic acid which encodes a mammalian beta-catenin.

The base sequences of the oligomers of the invention or of a region thereof are preferably at least 80% identical to a sequence selected from the group consisting of SEQ ID NOS: 1-132, such as at least 85%, at least 90%, at least 91%, at least 92%, at least 93%, at least 94%, at least 95%, at least 96%, at least 97%, at least 98%, at least 99%, even 100% identical.

The base sequences of the oligomers of the invention or of a region thereof are preferably at least 80% complementary to a sequence of a target region present in SEQ ID NO: 173, such as at least 85%, at least 90%, at least 91%, at least 92%, at least 93%, at least 94%, at least 95%, at least 96%, at least 97%, at least 98%, at least 99%, even 100% complementary.

In various embodiments, the sequence of the oligomer (or of a first region thereof) is selected from the group consisting of SEQ ID NOS: 1-132 or SEQ ID NOS: 174-193, or is selected from the group consisting of at least 10 contiguous monomers of SEQ ID NOS: 1-132 or SEQ ID NOS: 174-193. In another embodiment, the sequence of the oligomer of the invention or first region thereof optionally comprises 1, 2, or 3 base moieties that differ from those in SEQ ID NOs: 1-132 or SEQ ID NOs: 174-193, or at least 10 contiguous monomers thereof, when optimally aligned with said selected sequence or region thereof.

In certain embodiments, the monomer region consists of 11, 12, 13, 14, 15, 16, 17, 18, 19, 20, 21, 22, 23, 24, 25, 26, 27, 28, or 29 contiguous monomers, such as 10-15, 12-25, 12-22, such as 12-18 monomers. Suitably, in various embodiments, the region is of the same length as the oligomer of the invention.

In some embodiments, the oligomer comprises additional monomers at the 5' or 3' ends, such as, independently, 1, 2, 3, 4 or 5 additional monomers at the 5' end and/or the 3' end of the oligomer, which are non-complementary to the sequence of the target region. In various embodiments, the oligomer of the invention comprises a region that is complementary to the target, which is flanked 5' and/or 3' by additional monomers. In various embodiments, the 3' end of the region is flanked by 1, 2 or 3 DNA or RNA monomers. 3' DNA monomers are frequently used during solid state synthesis of oligomers. In various embodiments, which may be the same or different, the 5' end of the oligomer is flanked by 1, 2 or 3 DNA or RNA monomers. In certain embodiments, the additional 5' or 3' monomers are nucleosides, such as DNA or RNA monomers. In various embodiments, the additional 5' or 3' monomers may represent region D as referred to in the context of gapmer oligomers herein.

In certain embodiments, the oligomer according to the invention consists of, or comprises, contiguous monomers having a nucleobase sequence according to SEQ ID NO:1, or according to a region thereof.

In certain embodiments, the oligomer according to the invention consists of, or comprises, contiguous monomers having a nucleobase sequence according to SEQ ID NO:16, or according to a region thereof.

In certain embodiments, the oligomer according to the invention consists of, or comprises, contiguous monomers having a nucleobase sequence according to SEQ ID NO:17, or according to a region thereof.

In certain embodiments, the oligomer according to the invention consists of, or comprises, contiguous monomers having a nucleobase sequence according to SEQ ID NO:18, or according to a region thereof.

In certain embodiments, the oligomer according to the invention consists of, or comprises, contiguous monomers having a nucleobase sequence according to SEQ ID NO:33, or according to a region thereof.

In certain embodiments, the oligomer according to the invention consists of, or comprises, contiguous monomers having a nucleobase sequence according to SEQ ID NO:34, or according to a region thereof.

In certain embodiments, the oligomer according to the invention consists of, or comprises, contiguous monomers having a nucleobase sequence according to SEQ ID NO:49, or according to a region thereof.

In certain embodiments, the oligomer according to the invention consists of, or comprises, contiguous monomers having a nucleobase sequence according to SEQ ID NO:50, or according to a region thereof.

In certain embodiments, the oligomer according to the invention consists of, or comprises, contiguous monomers having a nucleobase sequence according to SEQ ID NO:51, or according to a region thereof.

In certain embodiments, the oligomer according to the invention consists of, or comprises, contiguous monomers having a nucleobase sequence according to SEQ ID NO:52, or according to a region thereof.

In certain embodiments, the oligomer according to the invention consists of, or comprises, contiguous monomers having a nucleobase sequence according to SEQ ID NO:53, or according to a region thereof.

In certain embodiments, the oligomer according to the invention consists of, or comprises, contiguous monomers having a nucleobase sequence according to SEQ ID NO:54, or according to a region thereof.

In certain embodiments, the oligomer according to the invention consists of, or comprises, contiguous monomers having a nucleobase sequence according to SEQ ID NO:55, or according to a region thereof.

In certain embodiments, the oligomer according to the invention consists of, or comprises, contiguous monomers having a nucleobase sequence according to SEQ ID NO:56, or according to a region thereof.

In certain embodiments, the oligomer according to the invention consists of, or comprises, contiguous monomers having a nucleobase sequence according to SEQ ID NO:57, or according to a region thereof.

In certain embodiments, the oligomer according to the invention consists of, or comprises, contiguous monomers having a nucleobase sequence according to SEQ ID NO:58, or according to a region thereof.

In certain embodiments, the oligomer according to the invention consists of, or comprises, contiguous monomers having a nucleobase sequence according to SEQ ID NO:73, or according to a region thereof.

In certain embodiments, the oligomer according to the invention consists of, or comprises, contiguous monomers having a nucleobase sequence according to SEQ ID NO:88, or according to a region thereof.

In certain embodiments, the oligomer according to the invention consists of, or comprises, contiguous monomers having a nucleobase sequence according to SEQ ID NO:103, or according to a region thereof.

In certain embodiments, the oligomer according to the invention consists of, or comprises, contiguous monomers having a nucleobase sequence according to SEQ ID NO:118, or according to a region thereof.

Sequence alignments can be used to identify regions of the nucleic acids encoding beta-catenin from human and one or more different mammalian species, such as monkey, mouse and/or rat, where there are sufficient stretches of nucleic acid identity between or among the species to allow the design of oligonucleotides which target (that is, which bind with sufficient specificity to inhibit expression of) both the human beta-catenin target nucleic acid and the corresponding nucleic acids present in the different mammalian species.

In some embodiments, such oligomers consist of or comprise regions of at least 10, such as at least 12, such as at least 14, such as at least 16, such as at least 18, such as 11, 12, 13, 14, 15, 16, 17 or 18 contiguous monomers which are 100% complementary in sequence to the sequence of the target regions of both the nucleic acid encoding beta-catenin from humans and of the nucleic acid(s) encoding beta-catenin from a different mammalian species.

In some embodiments, the oligomer of the invention comprises or consists of a region of contiguous monomers having a sequence that is at least 80%, such as at least 85%, such as at least 90%, such as at least 95%, such as at least 98%, or 100% complementary to the sequence of the target regions of both the nucleic acid encoding human beta-catenin and a nucleic acid(s) encoding beta-catenin from a different mammalian species, such as the mouse nucleic acid encoding beta-catenin. It is preferable that the contiguous nucleobase sequence of the oligomer is 100% complementary to the target region of the human beta-catenin mRNA.

Length

The oligomer comprises or consists of 10-50 contiguous monomers, such as 10, 11, 12, 13, 14, 15, 16, 17, 18, 19, 20, 21, 22, 23, 24, 25, 26, 27, 28, 29 or 30 contiguous monomers.

In various embodiments, the oligomers comprise or consist of 10-25 contiguous monomers, 12-25 or 10-22 contiguous monomers, such as 12-18 contiguous monomers, such as 13-17 or 12-16 contiguous monomers, such as 13, 14, 15, 16 contiguous monomers.

In various embodiments, the oligomers comprise or consist of 10, 11, 12, 13, or 14 contiguous monomers.

In various embodiments, the oligomer according to the invention consists of no more than 22 contiguous monomers, such as no more than 20 contiguous monomers, such as no more than 18 contiguous monomers, such as 15, 16 or 17 contiguous monomers. In certain embodiments, the oligomer of the invention comprises less than 20 contiguous monomers.

Nucleosides and Nucleoside Analogues

In various embodiments, at least one of the monomers present in the oligomer is a nucleoside analogue that contains a modified base, such as a base selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In various embodiments, at least one of the monomers present in the oligomer is a nucleoside analogue that contains a modified sugar.

In some embodiments, the linkage between at least 2 contiguous monomers of the oligomer is other than a phosphodiester bond.

In certain embodiments, the oligomer includes at least one monomer that has a modified base, at least one monomer (which may be the same monomer) having a modified sugar, and at least one inter-monomer linkage that is non-naturally occurring. Specific examples of nucleoside analogues useful in the oligomers described herein are described by e.g. Freier & Altmann; Nucl. Acid Res., 1997, 25, 4429-4443 and Uhlmann; Curr. Opinion in Drug Development; 2000, 3(2), 293-213, and in Scheme 1 (in which some nucleoside analogues are shown as nucleotides):

Scheme 1

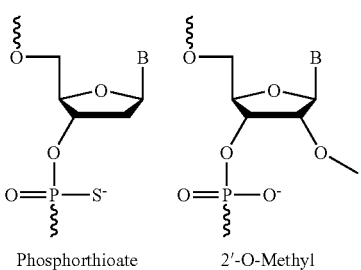

Phosphorthioate     2'-O-Methyl

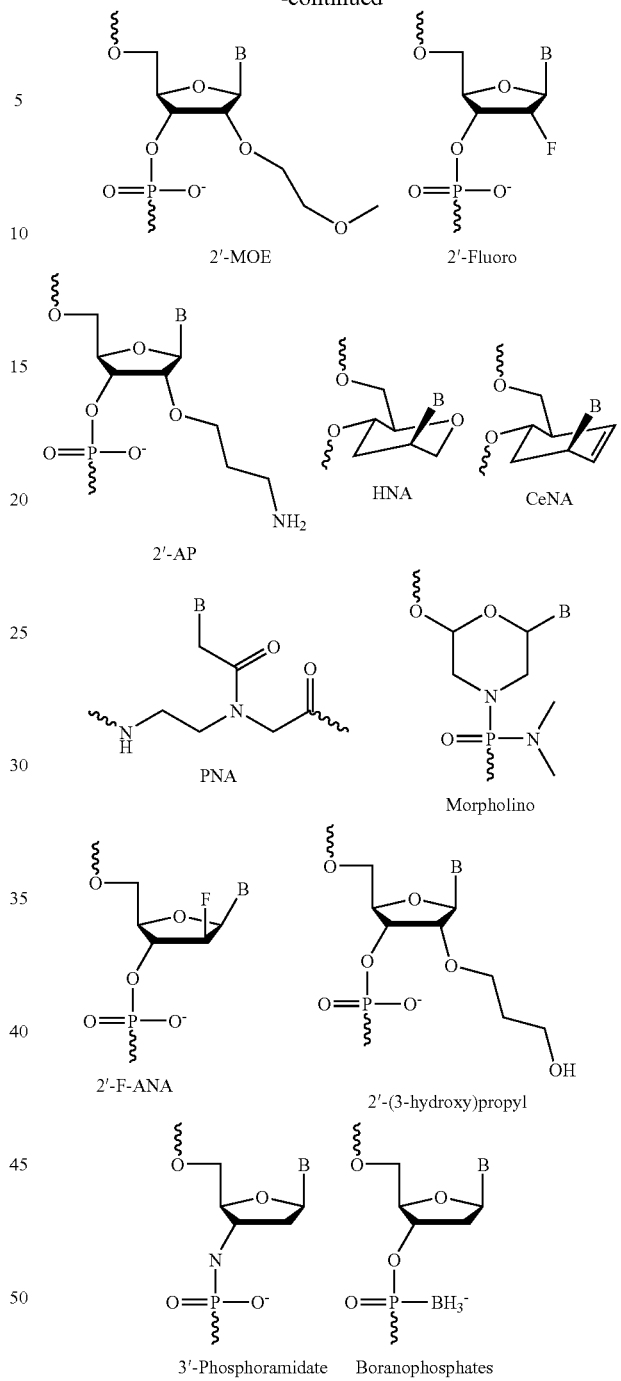

The oligomer may thus comprise or consist of a simple sequence of nucleosides—preferably DNA monomers, but also possibly RNA monomers, or a combination of nucleosides and one or more nucleoside analogues. In some embodiments, such nucleoside analogues suitably enhance the affinity of the oligomer for the target region of the target nucleic acid.

Examples of suitable and preferred nucleoside analogues are described in WO 2007/031091, incorporated herein by reference in its entirety, or are referenced therein.

In some embodiments, the nucleoside analogue comprises a sugar moiety modified to provide a 2'-substituent group, such as 2'-O-alkyl-ribose sugars, 2'-amino-deoxyribose sugars, and 2'-fluoro-deoxyribose sugars.

In some embodiments, the nucleoside analogue comprises a sugar in which a bridged structure, creating a bicyclic sugar (LNA), is present, which enhances binding affinity and may also provide some increased nuclease resistance. In various embodiments, the LNA monomer is selected from oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). In certain embodiments, the LNA monomers are beta-D-oxy-LNA. LNA monomers are further described, below.

Incorporation of affinity-enhancing nucleoside analogues in the oligomer, such as LNA monomers or monomers containing 2'-substituted sugars, can allow the size of the oligomer to be reduced, and may also reduce the upper limit to the size of the oligomer before non-specific or aberrant binding takes place.

In certain embodiments, the oligomer comprises at least 2 nucleoside analogues. In some embodiments, the oligomer comprises from 3-8 nucleoside analogues, e.g. 6 or 7 nucleoside analogues. In preferred embodiments, at least one of the nucleoside analogues is a locked nucleic acid (LNA) monomer; for example at least 3 or at least 4, or at least 5, or at least 6, or at least 7, or 8, of the nucleoside analogues are LNA monomers. In some embodiments all the nucleoside analogues are LNA monomers.

It will be recognised that when referring to a preferred oligomer base sequence, in certain embodiments the oligomers comprise a corresponding nucleoside analogue, such as a corresponding LNA monomer or other corresponding nucleoside analogue, which raise the duplex stability (Tm) of the oligomer/target region duplex (i.e. affinity enhancing nucleoside analogues).

In various preferred embodiments, any mismatches (that is, noncomplementarities) between the base sequence of the oligomer and the base sequence of the target region, if present, are located other than in the regions of the oligomer that contain affinity-enhancing nucleoside analogues (e.g., regions A or C), such as within region B as referred to herein below, and/or within region D as referred to herein below, and/or in regions of the oligomer containing only nucleosides, and/or in regions which are 5' or 3' to the region of the oligomer that is complementary to the target region.

In some embodiments the nucleoside analogues present within the oligomer of the invention (such as in regions A and C mentioned herein) are independently selected from, for example: monomers containing 2'-O-alkyl-ribose sugars, monomers containing 2'-amino-deoxyribose sugars, monomers containing 2'-fluoro-deoxyribose sugars, LNA monomers, monomers containing arabinose sugars ("ANA monomers"), monomers containing 2'-fluoro-ANA sugars, monomers containing d-arabino-hexitol sugars ("HNA monomers"), intercalating monomers as defined in Christensen, Nucl. Acids. Res. 30:4918-4925 (2002), hereby incorporated by reference, and monomers containing 2'MOE sugars. In certain embodiments, there is only one of the above types of nucleoside analogues present in the oligomer of the invention, or region thereof.

In certain embodiments, the nucleoside analogues contain 2'-O-methoxyethyl-ribose sugars (2'MOE), or 2'-fluoro-deoxyribose sugars or LNA sugars, and as such the oligonucleotide of the invention may comprise nucleoside analogues which are independently selected from these three types of analogue, or may comprise only one type of analogue selected from the three types. In certain oligomer embodiments containing nucleoside analogues, at least one of the nucleoside analogues contains a 2'-MOE-ribose sugar, such as 2, 3, 4, 5, 6, 7, 8, 9 or 10 nucleoside analogues containing 2'-MOE-ribose sugars. In certain embodiments, at least one of the nucleoside analogues contains a 2'-fluoro deoxyribose sugar, such as 2, 3, 4, 5, 6, 7, 8, 9 or 10 nucleoside analogues containing 2'-fluoro-deoxyribose sugars.

In various embodiments, the oligomer according to the invention comprises at least one Locked Nucleic Acid (LNA) monomer, such as 1, 2, 3, 4, 5, 6, 7, or 8 LNA monomers, such as 3-7 or 4-8 LNA monomers, or 3, 4, 5, 6 or 7 LNA monomers. In various embodiments, all of the nucleoside analogues are LNA monomers. In some embodiments, the oligomer comprises both beta-D-oxy-LNA monomers, and one or more of the following LNA units: thio-LNA monomers, amino-LNA monomers, oxy-LNA monomers, and/or ENA monomers in either the beta-D or alpha-L configuration or combinations thereof. In certain embodiments, the cytosine base moieties of all LNA monomers in the oligomer are 5-methylcytosines. In certain embodiments, of the invention, the oligomer comprises both LNA and DNA monomers. Typically, the combined total of LNA and DNA monomers is 10-25, preferably 10-20, even more preferably 12-16. In certain embodiments, of the invention, the oligomer, or a region thereof, consists of at least one LNA monomer, and the remaining monomers are DNA monomers. In certain embodiments, the oligomer comprises only LNA monomers and nucleosides (such as RNA or DNA monomers, most preferably DNA monomers), optionally linked with modified linkage groups such as phosphorothioate.

In various embodiments, at least one of the nucleoside analogues present in the oligomer has a modified base selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA monomer" refers to a nucleoside analogue containing a bicyclic sugar (an "LNA sugar"). The terms "LNA oligonucleotide" and "LNA oligomer" refer to an oligomer containing one or more LNA monomers.

The LNA monomer used in the oligomers of the invention preferably has the structure of the general formula I:

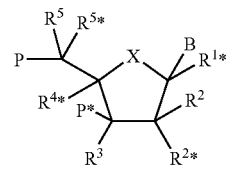

wherein X is selected from —O—, —S—, —N($R^{N*}$)—, —C($R^6R^{6*}$)—;

B is selected from hydrogen, optionally substituted $C_{1-4}$-alkoxy, optionally substituted $C_{1-4}$-, alkyl optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group;

$R^{4*}$ and $R^{2*}$ together designate a biradical consisting of 1-4 groups/atoms selected from —C ($R^a R^b$)—, —C($R^a$)=C ($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyn, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, -heteroaryl, heteroaryloxy-carbonyl, heteroaryloxy, heteroarylcarbonyl, amino, mono- and di($C_{1-6}$alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), and each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl -aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a Spiro biradical consisting of a 1-5 carbon atom(s) alkylene chain which is optionally interrupted and/or terminated by one or more heteroatoms/groups selected from —O—, —S—, and —(NR$^N$)— where $R^N$ is selected from hydrogen and $C_{1-4}$-alkyl, and where two adjacent (non-geminal) substituents may designate an additional bond resulting in a double bond; and $R^{N*}$ when present and not involved in a biradical, is selected from hydrogen and $C_{1-4}$-alkyl; and basic salts and acid addition salts thereof;

In certain embodiments, R5* is selected from H, —CH3, —CH2—CH3, —CH2—O—CH3, and —CH=CH2.

In various embodiments, R4* and R2 together designate a biradical selected from —C(RaRb)—O—, —C(RaRb)—C (RcRd)—O—, —C(RaRb)—C(RcRd)—C(ReRf)—O—, —C(RaRb)—O—C(RcRd)—, —C(RaRb)—O—C (RcRd)—O—, —C(RaRb)—C(RcRd)—, —C(RaRb)—C (RcRd)—C(ReRf)—, —C(Ra)=C(Rb)—, C(RcRd)—, —C(RaRb)—N(Rc)—, —C(RaRb)—C(RcRd)—N(Re)—, —C(RaRb)—N(Rc)—O—, and —C(RaRb)—S—, —C(RaRb)—C(RcRd)—S—, wherein Ra, Rb, Rc, Rd, Re, and Rf each is independently selected from hydrogen, optionally substituted C1-12-alkyl, optionally substituted C2-12-alkenyl, optionally substituted C2-12-alkynyl, hydroxy, C1-12-alkoxy, C2-12-alkoxyalkyl, C2-12-alkenyloxy, carboxy, C1-12-alkoxycarbonyl, C1-12-alkylcarbonyl, formyl, aryl, aryl-oxy-carbonyl, aryloxy, arylcarbonyl, heteroaryl, hetero-aryloxy-carbonyl, heteroaryloxy, heteroarylcarbonyl, amino, mono- and di(C1-6-alkyl)amino, carbamoyl, mono- and di(C1-6-alkyl)-amino-carbonyl, amino-C1-6-alkyl-aminocarbonyl, mono- and di(C1-6-alkyl)amino-C1-6-alkyl-aminocarbonyl, C1-6-alkyl-carbonylamino, carbamido, C1-6-alkanoyloxy, sulphono, C1-6-alkylsulphonyloxy, nitro, azido, sulphanyl, C1-6-alkylthio, halogen, DNA intercalators, photochemically active groups, thermochemically active groups, chelating groups, reporter groups, and ligands, where aryl and heteroaryl may be optionally substituted and where two geminal substituents Ra and Rb together may designate optionally substituted methylene (=CH2), In a further embodiment, R4* and R2* together designate a biradical selected from —CH2—O—, —CH2—S—, —CH2—NH—, —CH2—N(CH3)—, —CH2—CH2—O—, —CH2—CH(CH3)—, —CH2—CH2—S—, —CH2—CH2—NH—, —CH2—CH2—CH2—, —CH2—CH2—CH2—O—, —CH2—CH2—CH (CH3)—, —CH=CH—CH2—, —CH2—O—CH2—O—, —CH2—NH—O—, —CH2—N(CH3)—O—, —CH2O—CH2—, —CH(CH3)—O—, CH(CH2—O—CH3)—O—.

For all chiral centers, asymmetric groups may be found in either R or S orientation.

Preferably, the LNA monomer used in the oligomers of the invention comprises at least one LNA monomer according to any of the formulas

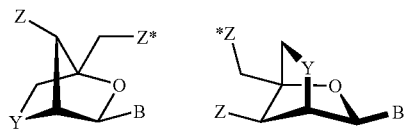

wherein Y is —O—, —O—CH$_2$—, —S—, —NH—, or N($R^H$); Z and Z* are independently selected among an internucleoside linkage, a terminal group or a protecting group; B constitutes an unmodified base moiety or a modified base moiety that either occurs naturally in nucleic acids or does not occur naturally in nucleic acids, and $R^H$ is selected from hydrogen and $C_{1-4}$-alkyl.

Specifically preferred LNA monomers are shown in Scheme 2:

Scheme 2

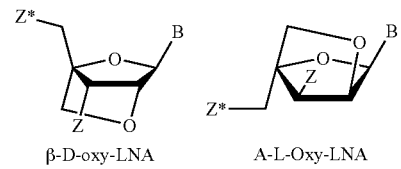

β-D-oxy-LNA          A-L-Oxy-LNA

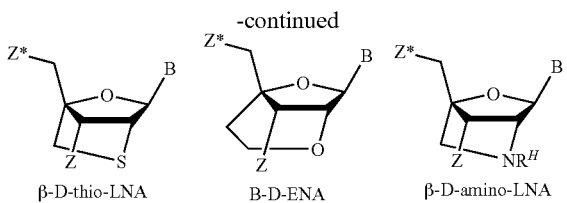

β-D-thio-LNA     B-D-ENA     β-D-amino-LNA

The term "thio-LNA" refers to an LNA monomer in which Y in the general formula above is selected from S or —CH2—S—. Thio-LNA can be in either the beta-D or alpha-L-configuration.

The term "amino-LNA" refers to an LNA monomer in which Y in the general formula above is selected from —N(H)—, N(R)—, CH2—N(H)—, and —CH2—N(R)— where R is selected from hydrogen and C1-4-alkyl. Amino-LNA can be in either the beta-D or the alpha-L-configuration.

The term "oxy-LNA" refers to an LNA monomer in which Y in the general formula above represents —O— or —CH2—O—. Oxy-LNA can be in either the beta-D or the alpha-L-configuration.

The term "ENA" refers to an LNA monomer in which Y in the general formula above is —CH2—O— (where the oxygen atom of —CH2—O— is attached to the 2'-position relative to the base B).

In a preferred embodiment, the LNA monomer is selected from a beta-D-oxy-LNA monomer, an alpha-L-oxy-LNA monomer, a beta-D-amino-LNA monomer and a beta-D-thio-LNA monomer, in particular a beta-D-oxy-LNA monomer.

In the present context, the term "C1-4-alkyl" means a linear or branched saturated hydrocarbon chain wherein the chain has from one to four carbon atoms, such as methyl, ethyl, n-propyl, isopropyl, n-butyl, isobutyl, sec-butyl and tert-butyl.

RNAse H Recruitment

It is recognised that an oligomer may function via non-RNase-mediated degradation of a target mRNA, such as by steric hindrance of translation, or other mechanisms; however, the preferred oligomers of the invention are capable of recruiting an endoribonuclease (RNase), such as RNase H.

Typically, the oligomer comprises a region of at least 6, such as at least 7, contiguous monomers, such as at least 8 or at least 9 contiguous monomers, including 7, 8, 9, 10, 11, 12, 13, 14, 15 or 16 contiguous monomers, which, when forming a duplex with the target region of the target RNA, is capable of recruiting RNase. The region of the oligomer which is capable of recruiting RNAse may be region B, as referred to in the context of a gapmer as described herein below. In certain embodiments, the region of the oligomer which is capable of recruiting RNAse, such as region B, consists of 10, 11, 12, 13, 14, 15, 16, 17, 18, 19 or 20 monomers.

EP 1 222 309 provides in vitro methods for determining RNaseH activity, which may be used to determine the ability of the oligomers of the invention to recruit RNaseH. An oligomer is deemed capable of recruiting RNase H if, when contacted with the complementary target region of the RNA target, it has an initial rate, as measured in pmol/l/min, of at least 1%, such as at least 5%, such as at least 10% or less than 20% of an oligonucleotide having the same base sequence but containing only DNA monomers, with no 2' substitutions, with phosphorothioate linkage groups between all monomers in the oligonucleotide, using the methodology provided by Example 91-95 of EP 1 222 309, incorporated herein by reference.

In various embodiments, an oligomer is deemed essentially incapable of recruiting RNaseH if, when contacted with the complementary target region of the RNA target, and RNaseH, the RNaseH initial rate, as measured in pmol/l/min, is less than 1%, such as less than 5%, such as less than 10% or less than 20% of the initial rate determined using an oligonucleotide having the same base sequence, but containing only DNA monomers, with no 2' substitutions, with phosphorothioate linkage groups between all monomers in the oligonucleotide, using the methodology provided by Example 91-95 of EP 1 222 309.

In other embodiments, an oligomer is deemed capable of recruiting RNaseH if, when contacted with the complementary target region of the RNA target, and RNaseH, the RNaseH initial rate, as measured in pmol/l/min, is at least 20%, such as at least 40%, such as at least 60%, such as at least 80% of the initial rate determined using an oligonucleotide having the same base sequence, but containing only DNA monomers, with no 2' substitutions, with phosphorothioate linkage groups between all monomers in the oligonucleotide, using the methodology provided by Example 91-95 of EP 1 222 309.

Typically, the region of the oligomer that forms a duplex with the complementary target region of the target RNA and is capable of recruiting RNase may contain DNA monomers and LNA monomers and may form a DNA/RNA like duplex with the target region. The LNA monomers are preferably in the alpha-L configuration, particularly preferred being alpha-L-oxy LNA.

The oligomer of the invention may comprise both nucleosides and nucleoside analogues, and may be in the form of a gapmer, a headmer or a mixmer.

A "headmer" is defined as an oligomer that comprises a first region and a second region that is contiguous thereto, with the 5'-most monomer of the second region linked to the 3'-most monomer of the first region. The first region comprises a contiguous stretch of non-RNase-recruiting nucleoside analogues, and the second region comprises a contiguous stretch (such as at least 7 contiguous monomers) of DNA monomers or nucleoside analogue monomers recognizable and cleavable by the RNAse.

A "tailmer" is defined as an oligomer that comprises a first region and a second region that is contiguous thereto, with the 5'-most monomer of the second region linked to the 3'-most monomer of the first region. The first region comprises a contiguous stretch (such as at least 7 such monomers) of DNA monomers or nucleoside analogue monomers recognizable and cleavable by the RNase, and the second region comprises a contiguous stretch of non-RNase recruiting nucleoside analogue monomers.

Other "chimeric" oligomers, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligomer for the target region, some nucleoside analogues also mediate RNase (e.g., RNase H) binding and cleavage. Since α-L-LNA monomers recruit RNase activity to a certain extent, in some embodiments, gap regions (e.g., region B as referred to herein below) of oligomers containing α-L-LNA monomers consist of fewer monomers recognizable and cleavable by the RNase, and more flexibility in the mixmer construction is introduced.

Gapmer Design

Preferably, the oligomer of the invention is a gapmer.

A "gapmer" is an oligomer which comprises a contiguous stretch of monomers capable of recruiting an RNAse, such as RNAseH, such as a region of at least 6 or 7 DNA monomers, referred to herein as region B, wherein region B is flanked both on its 5' and 3' ends by regions respectively referred to as regions A and C, each of regions A and C comprising or consisting of nucleoside analogues, such as affinity-enhancing nucleoside analogues, such as 1-6 nucleoside analogues.

Preferably the gapmer comprises regions, from 5' to 3', A-B-C, or optionally A-B-C-D or D-A-B-C, wherein: region A consists of or comprises at least one nucleoside analogue, such as at least one LNA monomer, such as 1-6 nucleoside analogues, such as LNA monomers; and region B consists of or comprises at least five contiguous monomers which are capable of recruiting RNAse (when formed in a duplex with a complementary target region of the target RNA molecule, such as the mRNA target), such as DNA monomers; and region C consists of or comprises at least one nucleoside analogue, such as at least one LNA monomer, such as 1-6 nucleoside analogues, such as LNA monomers, and; region D, when present, consists of or comprises 1, 2 or 3 monomers, such as DNA monomers.

In various embodiments, region A consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers; and/or region C consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers.

In certain embodiments, region B consists of or comprises 5, 6, 7, 8, 9, 10, 11 or 12 contiguous monomers which are capable of recruiting RNAse, or 6-10, or 7-9, such as 8 contiguous monomers which are capable of recruiting RNAse. In certain embodiments, region B consists of or comprises at least one DNA monomer, such as 1-12 DNA monomers, preferably 4-12 DNA monomers, more preferably 6-10 DNA monomers, such as 7-10 DNA monomers, most preferably 8, 9 or 10 DNA monomers.

In certain embodiments, region A consists of 3 or 4 nucleoside analogues, such as LNA monomers, region B consists of 7, 8, 9 or 10 DNA monomers, and region C consists of 3 or 4 nucleoside analogues, such as LNA monomers. Such designs include (A-B-C) 3-10-3, 3-104, 4-10-3, 3-9-3, 3-94, 4-9-3, 3-8-3, 3-8-4, 4-8-3, 3-7-3, 3-74, 4-7-3, and may further include region D, which may have one or 2 monomers, such as DNA monomers.

Further gapmer designs are disclosed in WO 2004/046160, which is hereby incorporated by reference.

U.S. provisional application 60/977,409, hereby incorporated by reference, refers to "shortmer" gapmer oligomers, which, in certain embodiments, may be the gapmer oligomer according to the invention.

In certain embodiments, the oligomer consists of 10, 11, 12, 13 or 14 contiguous monomers, wherein the regions of the oligomer have the pattern (5'-3'), A-B-C, or optionally A-B-C-D or D-A-B-C, wherein; region A consists of 1, 2 or 3 nucleoside analogue monomers, such as LNA monomers; region B consists of 7, 8 or 9 contiguous monomers which are capable of recruiting RNAse when formed in a duplex with a complementary RNA molecule (such as a mRNA target); and region C consists of 1, 2 or 3 nucleoside analogue monomers, such as LNA monomers. When present, region D consists of a single DNA monomer.

In certain embodiments, region A consists of 1 LNA monomer. In certain embodiments, region A consists of 2 LNA monomers. In certain embodiments, region A consists of 3 LNA monomers. In certain embodiments, region C consists of 1 LNA monomer. In certain embodiments, region C consists of 2 LNA monomers. In certain embodiments, region C consists of 3 LNA monomers. In certain embodiments, region B consists of 7 nucleoside monomers. In certain embodiments, B consists of 8 nucleoside monomers. In certain embodiments, region B consists of 9 nucleoside monomers. In certain embodiments, region B comprises 1-9 DNA monomers, such as 2, 3, 4, 5, 6, 7 or 8 DNA monomers. In certain embodiments, region B consists of DNA monomers. In certain embodiments, region B comprises at least one LNA monomer which is in the alpha-L configuration, such as 2, 3, 4, 5, 6, 7, 8 or 9 LNA monomers in the alpha-L-configuration. In certain embodiments, region B comprises at least one alpha-L-oxy LNA monomer or wherein all the LNA monomers in the alpha-L-configuration are alpha-L-oxy LNA monomers. In certain embodiments, the number of monomers present in the A-B-C regions of the oligomers is selected from the group consisting of (nucleotide analogue monomers—region B-nucleoside analogue monomers): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-94, or; 1-10-1, 1-10-2, 2-10-1, 2-10-2, 1-10-3, and 3-10-1. In certain embodiments, the number of monomers present in the A-B-C regions of the oligomers of the invention is selected from the group consisting of: 2-7-1, 1-7-2, 2-7-2, 3-7-3, 2-7-3, 3-7-2, 3-74, and 4-7-3. In certain embodiments, each of regions A and C consists of two LNA monomers, and region B consists of 8 or 9 nucleoside monomers, preferably DNA monomers.

Other gapmer designs include those where regions A and/or C consists of 3, 4, 5 or 6 nucleoside analogues, such monomers containing a 2'-O-methoxyethyl-ribose sugar (2'MOE) and monomers containing a 2'-fluoro-deoxyribose sugar, and region B consists of 8, 9, 10, 11 or 12 nucleosides, such as DNA monomers, where regions A-B-C have 5-10-5 or 4-12-4 monomers. Further gapmer designs are disclosed in WO 2007/146511A2, hereby incorporated by reference.

Linkage Groups

The monomers of the oligomer of the invention are coupled together via linkage groups. Suitably, each monomer is linked to the 3' adjacent monomer via a linkage group.

The terms "linkage group" or "internucleoside linkage" mean a group capable of covalently coupling together two contiguous monomers. Specific and preferred examples include phosphate groups (forming a phosphodiester between adjacent nucleoside monomers) and phosphorothioate groups (forming a phosphothioester between adjacent nucleoside monomers).

Suitable linkage groups include those listed within WO 2007/031091, for example the linkage groups listed on the first paragraph of page 34 of WO 2007/031091 (hereby incorporated by reference).

It is, in various embodiments, preferred to modify the linkage group from its normal phosphodiester to one that is more resistant to nuclease attack, such as phosphorothioate or boranophosphate—these two, being cleavable by RNase H, permitting RNase-mediated antisense inhibition of expression of the target gene.

Suitable sulphur (S) containing linkage groups as provided herein may be preferred. Phosphorothioate linkage groups are also preferred, particularly for the gap region (B) of gapmers. Phosphorothioate linkages may also be used for the flanking regions (A and C, and for linking A or C to D, and within region D, as appropriate).

Regions A, B and C, may however comprise linkage groups other than phosphorothioate, such as phosphodiester linkages, particularly, for instance when the use of nucleoside analogues protects the linkage groups within regions A and C from endo-nuclease degradation—such as when regions A and C comprise LNA monomers.

The linkage groups in the oligomer may be phosphodiester, phosphorothioate or boranophosphate so as to allow RNase H cleavage of the target RNA. Phosphorothioate is preferred, for improved nuclease resistance and other reasons, such as ease of manufacture.

In various embodiments, adjacent monomers of the oligomer are linked to each other by means of phosphorothioate groups.

It is recognised that the inclusion of phosphodiester linkages, such as one or two linkages, into an oligomer with a phosphorothioate backbone, particularly with phosphorothioate linkage groups between or adjacent to nucleoside analogue monomers (typically in region A and/or C), can modify the bioavailability and/or bio-distribution of an oligomer—see WO 2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleoside linkage groups are phosphorothioate.

When referring to specific gapmer oligonucleotide sequences, such as those provided herein, it will be understood that, in various embodiments, when the linkages are phosphorothioate linkages, alternative linkages, such as those disclosed herein, may be used, for example phosphate (phosphodiester) linkages may be used, particularly for linkages between nucleoside analogues, such as LNA monomers. Likewise, when referring to specific gapmer oligonucleotide sequences, such as those provided herein, when one or more of the cytosine bases is denoted as 5-methylcytosine, other cytosine bases present in the oligomer may be unmodified.

Oligomers

In certain embodiments, the oligomers of the invention are selected from the group consisting of: SEQ ID NO 133-152, as shown in Table 2.

In Table 2, upper case letters indicate nucleoside analogue monomers and subscript "s" represents a phosphorothioate linkage. Lower case letters represent nucleoside (DNA) monomers. Absence of "s" (if any) indicates a phosphodiester linkage.

TABLE 2

Oligomer designs

| SEQ ID NO | Sequence (5'-3') | Length (bases) |
|---|---|---|
| SEQ ID NO: 133 | $G_sA_sA_sa_sg_sc_st_sg_sa_st_sg_sg_sa_sC_sC_sA$ | 16 |
| SEQ ID NO: 134 | $C_sA_sG_sa_sc_st_st_sa_sa_sa_sg_sa_st_sG_sG_sC$ | 16 |
| SEQ ID NO: 135 | $C_sA_sG_sa_sa_st_sc_sc_sa_sc_st_sg_sg_sT_sG_sA$ | 16 |
| SEQ ID NO: 136 | $G_sC_sA_sc_st_sg_sc_sc_sa_st_st_st_sA_sG_sC$ | 16 |
| SEQ ID NO: 137 | $G_sT_sA_sa_st_sa_sg_sc_sa_sa_sg_sa_sA_sT_sT$ | 16 |
| SEQ ID NO: 138 | $A_sC_sT_sc_st_sg_sc_st_st_sg_st_sg_sg_sT_sC_sC$ | 16 |
| SEQ ID NO: 139 | $C_sC_sA_sc_sc_sa_sg_sc_st_st_sc_st_sa_sC_sA_sA$ | 16 |
| SEQ ID NO: 140 | $G_sA_sG_st_sc_sc_sa_sa_sa_sg_sa_sc_sa_sG_sT_sT$ | 16 |
| SEQ ID NO: 141 | $A_sC_sC_sc_sa_sc_st_st_sg_sg_sc_sa_sg_sA_sC_sC$ | 16 |
| SEQ ID NO: 142 | $G_sC_sA_sc_sa_sa_sa_sc_sa_sa_st_sg_sg_sA_sA_sT$ | 16 |
| SEQ ID NO: 143 | $G_sC_sA_sg_sC_st_sa_sc_st_sc_st_st_sG_sG_sA$ | 16 |
| SEQ ID NO: 144 | $C_sT_sC_sc_sc_st_sc_sa_sg_sc_st_st_sc_sA_sA_sT$ | 16 |
| SEQ ID NO: 145 | $G_sC_sA_sg_st_sc_st_sc_sa_st_sc_sc_sc_sA_sA_sG$ | 16 |
| SEQ ID NO: 146 | $T_sA_sT_sc_sc_sa_sc_sc_sa_sg_sa_sg_st_sG_sA_sA$ | 16 |
| SEQ ID NO: 147 | $C_sA_sT_sc_sc_sa_st_sg_sa_sg_sg_st_sc_sC_sT_sG$ | 16 |
| SEQ ID NO: 148 | $C_sC_sA_st_sc_st_st_sg_st_sg_sa_st_sc_sC_sA_sT$ | 16 |
| SEQ ID NO: 149 | $A_sA_sG_sc_sa_sa_sg_sc_sa_sa_sa_sg_st_sC_sA_sG$ | 16 |
| SEQ ID NO: 150 | $G_sA_sA_sa_st_st_sg_sc_st_sg_st_sa_sg_sC_sA_sG$ | 16 |
| SEQ ID NO: 151 | $G_sT_sG_st_st_sc_st_sa_sc_sa_sc_sc_sa_sT_sT_sA$ | 16 |
| SEQ ID NO: 152 | $A_sA_sC_sa_st_sg_sa_sa_sa_st_sa_sg_sa_sT_sC_sC$ | 16 |

Conjugates

In the context of this disclosure, the term "conjugate" indicates a compound formed by the covalent attachment ("conjugation") of an oligomer, as described herein, to one or more moieties that are not themselves nucleic acids or monomers ("conjugated moiety"). Examples of such conjugated moieties include macromolecular compounds such as proteins, fatty acid chains, sugar residues, glycoproteins, polymers, or combinations thereof. Typically, proteins may be antibodies for a target protein. Typical polymers may be polyethylene glycol. WO 2007/031091 provides suitable moieties and conjugates, which are hereby incorporated by reference.

Accordingly, provided herein are conjugates comprising an oligomer as herein described, and at least one conjugated moiety that is not a nucleic acid or monomer, covalently attached to said oligomer. Therefore, in certain embodiments, where the oligomer of the invention consists of contiguous monomers having a specified sequence of bases, as herein disclosed, the conjugate may also comprise at least one conjugated moiety that is covalently attached to said oligomer.

In certain embodiments, the oligomer is conjugated to a moiety that increases the cellular uptake of oligomeric compounds.

Conjugates may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

In certain embodiments, the conjugated moiety is a sterol, such as cholesterol.

In various embodiments, the conjugated moiety comprises or consists of a positively charged polymer, such as a positively charged peptide of, for example 1-50, such as 2-20 such as 3-10 amino acid residues in length, and/or polyalkylene oxide such as polyethylglycol(PEG) or polypropylene glycol—see WO 2008/034123, hereby incorporated by reference. Suitably, the positively charged polymer, such as a polyalkylene oxide may be attached to the oligomer of the invention via a linker such as the releasable inker described in WO 2008/034123.

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic NH2 group of the adenine base, a spacer that in some embodiments is hydrophilic and a terminal group that is capable of binding to a conjugated moiety (e.g., an amino, sulfhydryl or hydroxyl group). In some embodiments, this terminal group is not protected, e.g., is an NH2 group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl.

In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis.

In some embodiments, the oligomers are functionalized with a hindered ester containing an aminoalkyl linker, wherein the alkyl portion has the formula (CH2)w, wherein w is an integer ranging from 1 to 10, preferably about 6, wherein the alkyl portion of the alkylamino group can be straight chain or branched chain, and wherein the functional group is attached to the oligomer via an ester group (—O—C(O)—(CH2)wNH).

In other embodiments, the oligomers are functionalized with a hindered ester containing a (CH2)w-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—C(O)—CH2)wSH). In some embodiments, sulfhydryl-activated oligonucleotides are conjugated with polymer moieties such as polyethylene glycol or peptides (via formation of a disulfide bond).

Activated oligomers covalently linked to at least one functional moiety can be synthesized by any method known in the art, and in particular by methods disclosed in U.S. Patent Publication No. 2004/0235773, which is incorporated herein by reference in its entirety, and in Zhao et al. (2007) J. Controlled Release 119:143-152; and Zhao et al. (2005) Bioconjugate Chem. 16:758-766.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention have amine-containing functional moieties on the nucleobase, including on the N6 purine amino groups, on the exocyclic N2 of guanine, or on the N4 or 5 positions of cytosine. In some embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Compositions

The oligomer of the invention may be used in pharmaceutical formulations and compositions. Suitably, such compositions comprise a pharmaceutically acceptable diluent, carrier, salt or adjuvant WO 2007/031091 provides suitable and preferred pharmaceutically acceptable diluents, carriers and adjuvants—which are hereby incorporated by reference. Suitable dosages, formulations, administration routes, compositions, dosage forms, combinations with other therapeutic agents, pro-drug formulations are also provided in WO 2007/031091—which are also hereby incorporated by reference.

As used herein, the term "pharmaceutically acceptable salts" refers to salts that retain the desired biological activity of the herein identified compounds and exhibit acceptable levels of undesired toxic effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, /V,/V-dibenzylethylenediamine, D-glucosamine, tetraethylammonium, or ethylenediamine; or (c) combinations of (a) and (b); e.g., a zinc tannate salt or the like.

Applications

The term "treatment" as used herein refers to both treatment of an existing disease (e.g. a disease or disorder as referred to herein below), or prevention of a disease, i.e. prophylaxis. It will therefore be recognised that, in certain embodiments, "treatment" includes prophylaxis.

The oligomers of the invention may be utilized as research reagents for, for example, diagnostics, therapeutics and prophylaxis.

In research, such oligomers may be used to specifically inhibit the expression of beta-catenin protein (typically, by degrading or inhibiting beta-catenin mRNA and thereby preventing protein formation) in cells and experimental animals, thereby facilitating functional analysis of the target or an appraisal of its usefulness as a target for therapeutic intervention.

In diagnostics, the oligomers may be used to detect and quantitate beta-catenin expression in cells and tissues by northern blotting, in-situ hybridisation or similar techniques.

For therapeutics, a non-human animal or a human, suspected of having a disease or disorder which can be treated by modulating the expression of beta-catenin, is treated by administering an effective amount of an oligomer (or conjugate thereof) in accordance with this invention. Further provided are methods of treating a mammal, such as treating a human, suspected of having or being prone to a disease or condition, associated with expression of beta-catenin, by administering a therapeutically or prophylactically effective amount of one or more of the oligomers or compositions of the invention.

The invention also provides for the use of the compounds or conjugates of the invention as described for the manufacture of a medicament for the treatment of a disorder as referred to herein, or for a method of the treatment of a disorder as referred to herein.

The invention also relates to an oligomer, a composition or a conjugate as described herein for use as a medicament.

The invention also provides for a method for treating a disorder as referred to herein, the method comprising administering an effective amount of a compound according to the invention as herein described, and/or an effective amount of a conjugate according to the invention, and/or a pharmaceutical composition according to the invention to a patient in need thereof. In various embodiments, the oligomer, or conjugate thereof, induces a desired therapeutic effect in humans through, for example, hydrogen bonding to a target nucleic acid. The oligomer causes a decrease (inhibition) in the expression of a target via hydrogen bonding (hybridisation) to the mRNA of the target thereby re suiting in a reduction in gene expression. It is also envisaged that the oligomers and conjugates disclosed herein may have non-therapeutic applications, such as diagnostic applications.

It is highly preferred that the compounds of the invention are capable of hybridising to the target nucleic acid, such as beta-catenin mRNA, by Watson-Crick base pairing.

Medical Indications

In certain therapeutic embodiments, the disorder to be treated is selected from the group consisting of a hyperproliferative disorder, such as cancer, such as a cancer selected from the group consisting of colorectal cancer, hepatocellular cancer, endometrial cancer, malignant melanoma, ovarian cancer, pancreatic cancer, pituitary cancer, oesophageal cancer, lung cancer, breast cancer, kidney cancer, haematopoetic system cancer, cervical cancer, CNS cancer, bone cancer, biliary tract cancer and adrenal gland cancer In certain embodiments, the disorder, is a cancer selected from the group consisting of colorectal cancer, hepatocellular cancer, endometrial cancer, and malignant melanoma.

In certain embodiments, the disorder is a cancer selected from the group consisting of liver cancer and kidney cancer.

In certain embodiments, the disease or disorder is associated with a mutation in the beta-catenin gene or a gene whose protein product is associated with or interacts with beta-catenin, such as the APC gene. Therefore, in various embodiments, the target mRNA is a mutated form of the beta-catenin sequence, for example it may comprise one or more single point mutations, such as SNPs associated with cancer.

Examples of such diseases where mutations in the beta-catenin or APC gene lead to abnormal levels of beta-catenin activity are: (1) Colorectal cancer, APC and beta-catenin are mutually mutated in more than 70% of all cases (Powell et al., Nature, 1992; Morin et al., Science, 1997; Sparks et al., Cancer Res, 1998); (2) Hepatocellular cancer, beta-catenin are mutated in more than 25% of cases (de La Coste A, PNAS, 1998); (3) Endometrial cancer, beta-catenin are mutated >10%; and (4) Malignant melanoma, Beta-catenin are mutated >10% (Rubinfeld et al., Science, 1997).

Further examples of such diseases are cancer of the ovary, pancreas, pituitary, oesophagus, lung, breast, kidney, haematopoetic system, cervix, CNS, bone, biliary tract and adrenal gland. It has been shown that mutations in the beta-catenin or APC gene are associated with these diseases (Catalogue of Somatic Mutations in Cancer available from the Sanger Institute (United Kingdom) homepage http://www.sanger.ac.uk/).

In certain embodiments, the disease or disorder is associated with abnormal levels of a mutated form of beta-catenin. In certain embodiments, the disease or disorder is associated with abnormal levels of a wild-type form of beta-catenin. One aspect of the invention is directed to a method of treating a mammal suffering from or susceptible to conditions associated with abnormal levels of beta-catenin, comprising administering to the mammal a therapeutically effective amount of an oligomer of the invention targeted to beta-catenin or various compositions or conjugates thereof. In some embodiments, the oligomer comprises one or more LNA monomers.

Suitable dosages, formulations, administration routes, compositions, dosage forms, combinations with other therapeutic agents, pro-drug formulations are also provided in WO 2007/031091—which are hereby incorporated by reference. The invention also provides for a pharmaceutical composition comprising a compound or a conjugate as herein described or a conjugate, and a pharmaceutically acceptable diluent, carrier or adjuvant. WO 2007/031091 provides suitable and preferred pharmaceutically acceptable diluent, carrier and adjuvants—which are hereby incorporated by reference.

Furthermore, the invention described herein encompasses a method of preventing or treating a disease comprising administering a therapeutically effective amount of a beta-catenin modulating oligomer to a human in need of such therapy. The invention further encompasses the use of a short period of administration of a beta-catenin modulating oligonucleotide compound (oligomer or conjugate).

In various embodiments, the invention is drawn to a method of treating abnormal levels of beta-catenin comprising administering (i) an effective amount of a conjugate of the invention, or compositions thereof, and (ii) an effective amount of a second agent. In some embodiments, administration of the conjugate and the second agent is simultaneous. In other embodiments, administration of the conjugate and the second agent is sequential. Typically, the second agent is covalently linked to the oligomer to form the conjugate.

Further Embodiments

The following are further embodiments, and may be combined with the embodiments above-described, and embodiments set forth in the appended claims:

1. An antisense oligonucleotide (such as the oligomer) capable of binding to a target sequence of the beta-catenin gene of SEQ ID NO: 173 or all ele thereof and down-regulating expression of beta-catenin, said oligonucleotide comprising a sequence of 10-50 nucleobases corresponding to the target sequence.

2. The antisense oligonucleotide of embodiment 1, wherein the target sequence is selected from regions of the beta-catenin gene represented by SEQ ID NOS: 1-132 or an allelic variant thereof.

3. The oligonucleotide of embodiment 1 or embodiment 2 comprising a sequence of 10-16 nucleobases shown in SEQ ID NOS: 1, 16, 17, 18, 33, 34, 49, 50, 51, 52, 53, 54, 55, 56, 57, 58, 73, 88, 103, and 118 or an allelic variant thereof 4. The oligonucleotide according to any one of embodiments 1-3 comprising sequences shown as SEQ ID NOS: 1-132.

5. The oligonucleotide of any one of the preceding embodiments represented by SEQ ID NOS: 133-172.

6. The oligonucleotide according to any one of the preceding embodiments, wherein said nucleobase sequence comprises internucleobase linkages independently selected from phosphodiester, phosphorothioate and boranophosphate.

7. The oligonucleotide of any one of the preceding embodiments, wherein at least two of said nucleobases are nucleotide analogues.

8. The oligonucleotide according to embodiment 5, wherein said sequence of nucleobases comprises, in a 5' to 3' direction (i) region A: a stretch of 24 nucleotide analogues, followed by (ii) region B: a stretch of 6-11 nucleotides or nucleotide analogues different from those of region A, followed by (iii) region C: a stretch of 2-4 nucleotide analogues, and optionally followed by (iv) region D: one or two nucleotides.

9. The oligonucleotide according to embodiment 8, wherein the region A comprises at least one phosphodiester linkage between two nucleotide analogue units and/or or a nucleotide analogue unit and a nucleobase unit of Region B.

10. The oligonucleotide according to embodiment 8 or embodiment 9, wherein region C comprises at least one phosphodiester linkage between two nucleotide analogue units and/or a nucleotide analogue unit and a nucleobase unit of Region B.

11. The oligonucleotide according to any one of embodiments 1 to 6, wherein all the internucleobase linkages are phosphorothioate.

12. The oligonucleotide according to any one of embodiments 7 to 11, wherein said nucleotide analogue units are independently selected from 2'-O-alkyl-RNA, 2'-amino-DNA, 2'-fluoro-DNA, locked nucleic acid (LNA), arabino nucleic acid (ANA), 2'-fluoro-ANA, HNA, INA and 2'-MOE.

13. The oligonucleotide according to embodiment 12, wherein the nucleotide analogues are independently selected from 2'-MOE-RNA, 2'-fluoro-DNA, and LNA.

14. The oligonucleotide according to embodiment 13, wherein at least one of said nucleotide analogues is a locked nucleic acid (LNA).

15. The oligonucleotide according to embodiment 14, wherein all the nucleotide analogues are LNA.

16. The oligonucleotide according to any one of embodiments 12 to 15, wherein LNA is selected from beta-D-oxy-LNA, alpha-L-oxy-LNA, beta-D-amino-LNA and beta-D-thio-LNA.

17. A conjugate comprising an oligonucleotide of any one of the preceding embodiments and at least one non-nucleotide or non-polynucleotide moiety covalently attached to said oligonucleotide.

18. A conjugate according to embodiment 17, wherein said non-nucleotide or non-polynucleotide moiety consists of or comprises a sterol group such as cholesterol.

19. A pharmaceutical composition comprising an oligonucleotide according to any one of the embodiments 1 to 16 or a conjugate according to embodiment 17 or embodiment 18, and a pharmaceutically acceptable diluent, carrier or adjuvant.

20. An oligonucleotide or a conjugate according to any one of embodiments 1 to 18 for use as a medicament.

21. Use of an oligonucleotide or as conjugate according to any one of embodiments 1 to 18 for the manufacture of a medicament for the treatment of abnormal levels of beta-catenin or a disease or condition for which down-regulation of beta-catenin expression is indicated.

22. The use according to embodiment 21, wherein said disease or condition is cancer.

23. A method of treating a subject suffering from cancer, the method comprising the step of administering a pharmaceutical composition, oligonucleotide or conjugate according to any one of embodiments 1 to 19 to the subject in need thereof.

24. The use or the method of any one of embodiments 21-23, wherein the cancer is selected from colorectal cancer, hepatocellular cancer, endometrial cancer, malignant melanoma, cancer of the ovary, pancreas, pituitary, oesophagus, lung, breast, kidney, haematopoetic system, cervix, CNS, bone, biliary tract and adrenal gland.

25. A target sequence within the beta-catenin gene, wherein an antisense oligonucleotide corresponding to said target sequence is capable of down-regulating the expression of beta-catenin.

26. The target sequence of embodiment 25, wherein the target sequence is selected from the regions of the beta-catenin gene complementary to SEQ ID NOs 1-132 or allelic variants thereof.

27. A method of down-regulating the expression of beta-catenin in a cell, comprising contacting the cell with an oligonucleotide according to any one of embodiments 1-16.

7. EXAMPLES

Example 1

Monomer Synthesis

The LNA monomer building blocks and derivatives were prepared following published procedures and references cited therein—see WO 07/031,081 and the references cited therein.

Example 2

Oligonucleotide Synthesis

Oligonucleotides were synthesized according to the method described in WO 07/031,081. Table 1 shows examples of antisense oligonucleotide motifs and of the invention.

Example 3

Design of the Oligonucleotides

In accordance with the invention, a series of oligonucleotides were designed to target different regions of the human beta-atenin mRNA using the published sequence, GenBank accession number NM_001904, presented herein as SEQ ID NO: 173.

Table 2 shows oligomer designs of the invention. Table 3 shows 24 mer sequence motifs from which oligomers of the invention may be designed—the bold type represents 16 mer sequence motifs as shown in Table 1 that are incorporated into the longer oligomers.

TABLE 3

Beta-Catenin 24mers Sequences

| 16mer SEQ IDs | Short-mer SEQ IDs | Compound IDs | 24mer SEQ IDs | 24-mer SEQ ID |
|---|---|---|---|---|
| SEQ ID NO: 1 | 2-15 | 133-153 | ttagaaagctgatggaccataac | 174 |
| SEQ ID NO: 16 | | 134-154 | cctccagacttaaagatggccagt | 175 |
| SEQ ID NO: 17 | | 135-155 | aacacagaatccactggtgaacca | 176 |
| SEQ ID NO: 18 | 19-32 | 136-156 | aaacgcactgccattttagctcct | 177 |
| SEQ ID NO: 33 | | 137-157 | tgtcgtaatagccaagaatttaac | 178 |
| SEQ ID NO: 34 | 35-48 | 138-158 | cagcactctgcttgtggtccacag | 179 |
| SEQ ID NO: 49 | | 139-159 | cattccaccagcttctacaatagc | 180 |
| SEQ ID NO: 50 | | 140-160 | ctgagagtccaaagacagttctga | 181 |
| SEQ ID NO: 51 | | 141-161 | taccacccacttggcagaccatca | 182 |
| SEQ ID NO: 52 | | 142-162 | agctgcacaaacaatggaatggta | 183 |
| SEQ ID NO: 53 | | 143-163 | ccctgcagctactctttggatgtt | 184 |
| SEQ ID NO: 54 | | 144-164 | gtggctccctcagcttcaatagct | 185 |
| SEQ ID NO: 55 | | 145-165 | atcagcagtctcattccaagccat | 186 |

TABLE 3-continued

Beta-Catenin 24mers Sequences

| 16mer SEQ IDs | Short-mer SEQ IDs | Compound IDs | 24mer SEQ IDs | 24-mer SEQ ID |
|---|---|---|---|---|
| SEQ ID NO: 56 | | 146-166 | gccatatccaccagagtgaaaaga | 187 |
| SEQ ID NO: 57 | | 147-167 | agcccatccatgaggtcctgggca | 188 |
| SEQ ID NO: 58 | 59-72 | 148-168 | aattccatcttgtgatccattctt | 189 |
| SEQ ID NO: 73 | 74-87 | 149-169 | ttcaaagcaagcaaagtcagtacc | 190 |
| SEQ ID NO: 88 | 89-102 | 150-170 | attagaaattgctgtagcagtatt | 191 |
| SEQ ID NO: 103 | 104-117 | 151-171 | attagtgttctacaccattactca | 192 |
| SEQ ID NO: 118 | 119-132 | 152-172 | caaaaacatgaaatagatccacct | 193 |

Example 4

In Vitro Model: Cell Culture

The effect of antisense oligonucleotides on target nucleic acid expression can be tested in any of a variety of cell types provided that the target nucleic acid is present at measurable levels. Target nucleic acids can be expressed endogenously or by transient or stable transfection. The expression level of the target nucleic acid can be routinely determined using, for example, Northern blot analysis, Real-Time PCR, Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% CO2. Cells were routinely passaged 2-3 times weekly.

SW480: The human colorectal cancer cell line SW480 was cultured in L-15 medium (Leibovitz)+10% fetal bovine serum (FBS)+Glutamax I+pen/strep.

HCT116: The human colorectal cancer cell line HCT116 was cultured in McCoy's 5a modified medium (Sigma)+10% fetal bovine serum (FBS)+Glutamax I+pen/strep.

Example 5

In Vitro Model: Treatment with Antisense Oligonucleotide

The cells were treated with oligonucleotide using the cationic liposome formulation LipofectAMINE 2000 (Gibco) as transfection vehicle. Cells were seeded in 6-well cell culture plates (NUNC) and treated when 75-90% confluent. Oligonucleotide concentrations used ranged from 1 nM to 25 nM final concentration. Formulation of oligonucleotide-lipid complexes were carried out essentially as described by the manufacturer using serum-free OptiMEM (Gibco) and a final lipid concentration of 10 µg/mL LipofectAMINE 2000. Cells were incubated at 37° C. for 4 hours and treatment was stopped by removal of oligonucleotide-containing culture medium. Cells were washed and serum-containing media was added. After oligonucleotide treatment cells were allowed to recover for 20 hours before they were harvested for RNA analysis.

Example 6

In Vitro Model: Extraction of RNA and cDNA Synthesis

For RNA isolation from the cell lines, the RNeasy mini kit (Qiagen cat. no. 74104) was used according to the protocol provided by the manufacturer.

First strand synthesis was performed using Reverse Transcriptase reagents from Ambion according to the manufacturer's instructions.

For each sample 0.5 µg total RNA was adjusted to 10.8 µl with RNase free H2O and mixed with 2 µl random decamers (50 µM) and 4 µl dNTP mix (2.5 mM each dNTP) and heated to 70° C. for 3 min after which the samples were rapidly cooled on ice. After cooling the samples on ice, 2 µl 10× Buffer RT, 1 µl MMLV Reverse Transcriptase (100 U/µl) and 0.25 µl RNase inhibitor (10 U/µl) was added to each sample, followed by incubation at 42° C. for 60 min, heat inactivation of the enzyme at 95° C. for 10 min and then the sample was cooled to 4° C.

Example 7

In Vitro Model: Analysis of Oligonucleotide Inhibition of Beta-Catenin Expression by Real-Time PCR Antisense modulation of beta-catenin expression can be assayed in a variety of ways known in the art. For example, beta-catenin mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA. Methods of RNA isolation and RNA analysis such as Northern blot analysis is routine in the art and is taught in, for example, Current Protocols in Molecular Biology, John Wiley and Sons.

Real-time quantitative (PCR) can be conveniently accomplished using the commercially available Multi-Color Real Time PCR Detection System, available from Applied Biosystem.

7.2.1 Real-Time Quantitative PCR Analysis of Beta-Catenin mRNA Levels

The sample content of human beta-catenin mRNA was quantified using the human beta-catenin ABI Prism Pre-Developed TaqMan Assay Reagent (Applied Biosystems cat. no. HS00170025_m1) according to the manufacturer's instructions.

Glyceraldehyde-3-phosphate dehydrogenase (GAPDH) mRNA quantity was used as an endogenous control for normalizing any variance in sample preparation.

The sample content of human GAPDH mRNA was quantified using the human GAPDH ABI Prism Pre-Developed TaqMan Assay Reagent (Applied Biosystems cat. no. 4310884E) according to the manufacturer's instructions.

Real-time Quantitative PCR is a technique well known in the art and is taught in for example Heid et al. Real time quantitative PCR, Genome Research (1996), 6: 986-994.

7.2.2 Real Time PCR

The cDNA from the first strand synthesis performed as described in Example 8 was diluted 2-20 times, and analyzed by real time quantitative PCR using Taqman 7500 FAST from Applied Biosystems. The primers and probe were mixed with 2× Taqman Fast Universal PCR master mix (2×) (Applied Biosystems Cat.# 436-4103) and added to 4 µl cDNA to a final volume of 10 µl. Each sample was analysed in triplicate. Assaying 2 fold dilutions of a cDNA that had been prepared on material purified from a cell line expressing the RNA of interest generated standard curves for the assays. Sterile H2O was used instead of cDNA for the no template control. PCR program: 95° C. for 30 seconds, followed by 40 cycles of 95° C., 3 seconds, 60° C., 30 seconds. Relative quantities of target mRNA sequence were determined from the calculated Threshold cycle using the Applied Biosystems Fast System SDS Software Version 1.3.1.21.

7.2.3 Example 8

In Vitro Analysis: Antisense Inhibition of Human Beta-Catenin Expression by Oligonucleotides Oligonucleotides from Table 2 were evaluated for their potential to knockdown beta-catenin mRNA at concentrations of 1, 5, and 25 nM in SW480 cells (see FIG. 2). Results are tabulated in Table 4, in which the data are presented as percentage down-regulation of beta-catenin mRNA relative to mock transfected cells at 5 nM. Lower case letters represent DNA monomers, bold upper case letters represent β-D-oxy-LNA monomers. The cytosine bases of all LNA monomers are 5'methyl cytosines. Subscript "s" represents phosphorothiate linkage.

TABLE 4

| Test Substance | Sequence (5'-3') | Beta-catenin (% inhib.) |
|---|---|---|
| SEQ ID NO: 153 | G$_s$A$_s$A$_s$a$_s$g$_s$c$_s$t$_s$g$_s$a$_s$t$_s$g$_s$g$_s$a$_s$C$_s$C$_s$A | 88.11% |
| SEQ ID NO: 154 | C$_s$A$_s$G$_s$a$_s$c$_s$t$_s$t$_s$a$_s$a$_s$a$_s$g$_s$a$_s$t$_s$G$_s$G$_s$C | 86.4% |
| SEQ ID NO: 155 | C$_s$A$_s$G$_s$a$_s$a$_s$t$_s$c$_s$c$_s$a$_s$c$_s$t$_s$g$_s$g$_s$T$_s$G$_s$A | 76.6% |
| SEQ ID NO: 156 | G$_s$C$_s$A$_s$c$_s$t$_s$g$_s$c$_s$c$_s$a$_s$t$_s$t$_s$t$_s$t$_s$A$_s$G$_s$C | 89.2% |
| SEQ ID NO: 157 | T$_s$T$_s$A$_s$a$_s$t$_s$a$_s$g$_s$c$_s$c$_s$a$_s$a$_s$g$_s$a$_s$A$_s$T$_s$T | 56.4% |
| SEQ ID NO: 158 | A$_s$C$_s$T$_s$c$_s$t$_s$g$_s$c$_s$t$_s$t$_s$g$_s$t$_s$g$_s$g$_s$T$_s$C$_s$C | 77.6% |
| SEQ ID NO: 159 | C$_s$C$_s$A$_s$c$_s$c$_s$a$_s$g$_s$c$_s$t$_s$c$_s$t$_s$a$_s$C$_s$A$_s$A | 49.7% |
| SEQ ID NO: 160 | G$_s$A$_s$G$_s$t$_s$c$_s$c$_s$a$_s$a$_s$a$_s$g$_s$a$_s$c$_s$a$_s$G$_s$T$_s$T | 60.1% |
| SEQ ID NO: 161 | A$_s$C$_s$C$_s$c$_s$a$_s$c$_s$t$_s$t$_s$g$_s$g$_s$c$_s$a$_s$g$_s$A$_s$C$_s$C | 75.6% |
| SEQ ID NO: 162 | G$_s$C$_s$A$_s$c$_s$a$_s$a$_s$a$_s$c$_s$a$_s$a$_s$t$_s$g$_s$g$_s$A$_s$A$_s$T | 10.8% |
| SEQ ID NO: 163 | G$_s$C$_s$A$_s$g$_s$c$_s$t$_s$a$_s$c$_s$t$_s$c$_s$t$_s$t$_s$t$_s$G$_s$G$_s$A | 48.3% |
| SEQ ID NO: 164 | C$_s$T$_s$C$_s$c$_s$c$_s$t$_s$c$_s$a$_s$g$_s$c$_s$t$_s$c$_s$A$_s$A$_s$T | 35.5% |
| SEQ ID NO: 165 | G$_s$C$_s$A$_s$g$_s$t$_s$c$_s$t$_s$c$_s$a$_s$t$_s$t$_s$c$_s$c$_s$A$_s$A$_s$G | 25.5% |
| SEQ ID NO: 166 | T$_s$A$_s$T$_s$c$_s$c$_s$a$_s$c$_s$c$_s$a$_s$g$_s$a$_s$g$_s$t$_s$G$_s$A$_s$A | 27.3% |
| SEQ ID NO: 167 | C$_s$A$_s$T$_s$c$_s$c$_s$a$_s$t$_s$g$_s$a$_s$g$_s$g$_s$t$_s$c$_s$C$_s$T$_s$G | 24.5% |
| SEQ ID NO: 168 | C$_s$C$_s$A$_s$t$_s$c$_s$t$_s$t$_s$g$_s$t$_s$g$_s$a$_s$t$_s$c$_s$C$_s$A$_s$T | 74.4% |
| SEQ ID NO: 169 | A$_s$A$_s$G$_s$c$_s$a$_s$a$_s$g$_s$c$_s$a$_s$a$_s$a$_s$g$_s$t$_s$C$_s$A$_s$G | 87.5% |
| SEQ ID NO: 170 | G$_s$A$_s$A$_s$a$_s$t$_s$t$_s$g$_s$c$_s$t$_s$g$_s$t$_s$a$_s$g$_s$C$_s$A$_s$G | 91.5% |
| SEQ ID NO: 171 | G$_s$T$_s$G$_s$t$_s$t$_s$c$_s$t$_s$a$_s$c$_s$a$_s$c$_s$c$_s$a$_s$T$_s$T$_s$A | 94.9% |
| SEQ ID NO: 172 | A$_s$A$_s$C$_s$a$_s$t$_s$g$_s$a$_s$a$_s$a$_s$t$_s$a$_s$g$_s$a$_s$T$_s$C$_s$C | 93.6% |
| SEQ ID NO: 194 | C$_s$G$_s$T$_s$c$_s$a$_s$g$_s$t$_s$a$_s$t$_s$g$_s$c$_s$g$_s$A$_s$A$_s$T$_s$c | |

As shown in Table 4, oligonucleotides of SEQ ID NOs: 153, 154, 155, 156, 158, 161, 168, 169, 170, 171 and 172 demonstrated about 74% or greater inhibition of beta-catenin mRNA expression at 5 nM in these experiments and are therefore preferred.

Also preferred are oligonucleotides based on the illustrated antisense oligomer sequences, for example varying the length (shorter or longer) and/or monomer content (e.g. the type and/or proportion of nucleoside analogue monomers), which also provide good inhibition of beta-catenin expression.

7.2.4 Example 9

In Vitro Analysis: Western Blot Analysis of Beta-Catenin Protein Levels

The in vitro effect of oligomeric compounds on beta-catenin protein levels in transfected cells was determined by Western Blotting. 200.000 SW480 cells transfected with oligonucleotides as described in Example 5 were harvested and lysed in RIPA lysis buffer (50 mM Tris-HCl pH7.4, 150 mM NaCl, 1 mM EDTA, 1% Triton X-100, 0.1% SDS, 1% Sodium Deoxycholate) supplemented with protease inhibitor cocktail (Roche). Total protein concentrations were measured using a BCA protein assay kit (Pierce). 50 µg total protein was run on 3-8% Tris Acetate gels and blotted onto PVDF membranes according to manufacturer's instructions (Invitrogen). After overnight incubation in blocking buffer (PBS-T supplemented with 5% low fat milk powder), the membranes were incubated overnight with an anti-beta-catenin antibody (BD Transduction laboratories). As control of loading tubulin was detected using monoclonal antibodies from Neomarker. Membranes were then incubated with secondary antibodies and Beta-catenin or tubulin proteins were visualized using a chemiluminescence ECL+detection kit (Amersham). See FIG. 3.

7.2.5 Example 10

Measurement of Proliferating Viable Cells (MTS Assay)

HCT116 colorectal cancer cells were seeded to a density of 200,000 cells per well in a 6 well plate in McCoy's 5a modified medium (Sigma M8403)+2 mM Glutamax I (Gibco 35050-038)+10% FBS (Brochrom #193575010)+25 µg/µl Gentarnicin (Sigma G1397 50 mg/ml) the day prior to transfection. The next day medium was removed followed by addition of 1.2 ml OptiMEM containing 7.5 µg/ml Lipofectamine 2000 (Invitrogen). Cells were incubated for 7 min before adding 0.3 ml oligonucleotides diluted in OptiMEM. The final oligonucleotide concentration was 25 nM. After 4 hours of treatment, media was removed and cells were trypsinized and seeded to a density of 5000 cells per well in clear 96 well plates (Scientific Orange no. 1472030100) in 100 µl McCoy's 5a modified medium (Sigrma M8403)+2 mM Glutamax I (Gibco 35050-038)+10% FBS (Brochrom #193575010)+25 µg/µl Gentamicin (Sigma G1397 50 mg/ml). Viable cells were measured at the times indicated by adding 10 µl the tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES) (CellTiter 96® AQueous One Solution Cell Proliferation Assay, Promega). Viable cells were measured at 490 nm in a Powerwave (Biotek Instruments). The OD490 nm were plotted against time/h. (See FIG. 4).

7.2.6 Example 11

Inhibition of Beta-Catenin mRNA in Mouse Liver

NMRI mice were dosed i.v. with 25 mg/kg oligonucleotide (SEQ ID NO: 156, 158, 168, 169, 171) on three consecutive days (group size of 5 mice). The antisense oligonucleotides were dissolved in 0.9% saline (NaCl). Animals were sacrificed 24 h after last dosing and liver tissue was sampled and stored in RNA later until RNA extraction and QPCR analysis. Total RNA was extracted and beta-catenin mRNA expression in liver samples was measured by QPCR as described in Example 7 using a mouse beta-catenin QPCR assay (cat. Mm00483033_ml, Applied Biosystems). Results were normalised to mouse GAPDH (cat. no. 4352339E, Applied Biosystems) and plotted relative to saline treated controls, see FIG. 5.

7.2.7 Example 12

Preparation of a Conjugate of SEQ ID NO: 161 and Polyethylene Glycol

The oligomers having SEQ ID NO: 161, SEQ ID NO: 168 and SEQ ID NO: 171 are functionalized on the 5' terminus by attaching an aminoalkyl group, such as hexan-1-amine blocked with a blocking group such as Fmoc to the 5' phosphate groups of the oligomers using routine phosphoramidite chemistry, oxidizing the resultant compounds, deprotecting them and purifying them to achieve the functionalized oligomers, respectively, having the formulas (IA), (IB) and (IC):

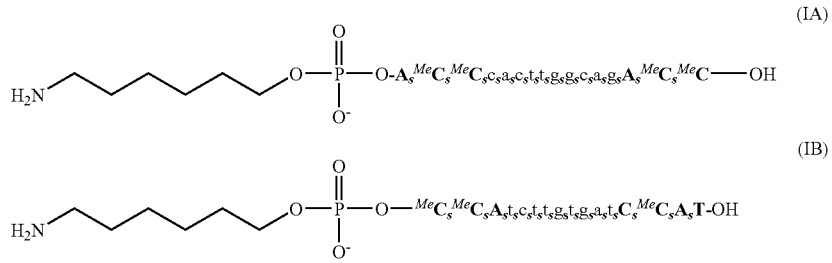

-continued (IC)

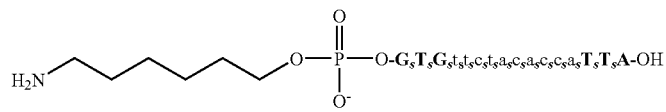

wherein the bold capital letters and the subscript "s" in SEQ ID NOs: 161, 168 and 171 have the same meaning as discussed above, and MeC is 5-methylcytosine.

A solution of activated PEG, such as the one shown in formula (II):

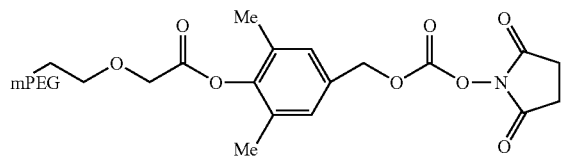

wherein the PEG moiety has an average molecular weight of 12,000, and each of the compounds of formulas (IA), (IB) and (C) in PBS buffer are stirred in separate vessels at room temperature for 12 hours. The reaction solutions are extracted three times with methylene chloride and the combined organic layers are dried over magnesium sulphate and filtered and the solvent is evaporated under reduced pressure. The resulting residues are dissolved in double distilled water and loaded onto an anion exchange column. Unreacted PEG linker is eluted with water and the products are eluted with NH4HCO3 solution. Fractions containing pure products are pooled and lypophitized to yield the conjugates SEQ ID NOs: 161, 168 and 171, respectively as show in formulas (IIIA), (IIIB) and (IIIC):

(IIIA)

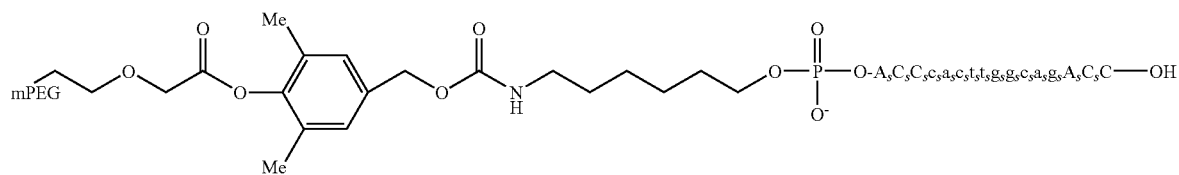

(IIIB)

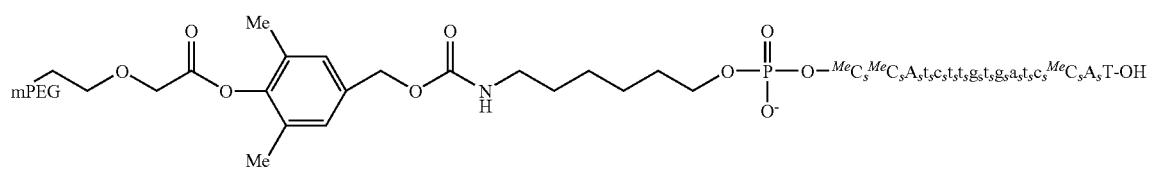

(IIIC)

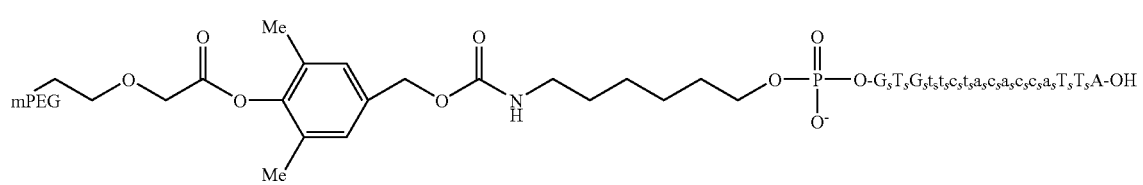

wherein each of the oligomers of SEQ ID NOs: 161, 168 and 171 is attached to a PEG polymer having average molecular weight of 12,000 via a linker.

8. SPECIFIC EMBODIMENTS, CITATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein; the disclosure of each such reference is hereby incorporated herein by reference in its entirety.

What is claimed is:

1. An The oligomer consisting of the formula:
5'-$G_sT_sG_st_st_sc_st_sa_sc_sa_sc_sc_sa_sT_sT_sA$-3' (SEQ ID NO: 171), wherein uppercase letters denote beta-D-oxy-LNA monomers, lowercase letters denote DNA monomers, and the subscript "s" denotes a phosphorothioate linkage.

2. A conjugate comprising the oligomer according to claim 1 covalently attached to at least one moiety that is not a nucleic acid or a monomer.

3. A pharmaceutical composition comprising the oligomer according to claim 1 and a pharmaceutically acceptable diluent, carrier, salt, or adjuvant.

4. An activated oligomer consisting of the oligomer of claim 1 and at least one functional group covalently attached thereto at one or more positions independently selected from the 5'-end, the 3' end, the 2'-OH of a ribose sugar, and the base.

5. A pharmaceutical composition comprising the conjugate according to claim 2 and a pharmaceutically acceptable diluent, carrier, salt or adjuvant.

* * * * *

UNITED STATES PATENT AND TRADEMARK OFFICE
CERTIFICATE OF CORRECTION

| | | |
|---|---|---|
| PATENT NO. | : 7,915,401 B2 | Page 1 of 1 |
| APPLICATION NO. | : 12/356923 | |
| DATED | : March 29, 2011 | |
| INVENTOR(S) | : Jesper Worm | |

It is certified that error appears in the above-identified patent and that said Letters Patent is hereby corrected as shown below:

Claim 1, Column 185, line 2, should read as follows:

-- 1. An oligomer consisting of the formula: --.

Signed and Sealed this
Tenth Day of January, 2012

David J. Kappos
*Director of the United States Patent and Trademark Office*

```
                       SEQUENCE LISTING

<160> NUMBER OF SEQ ID NOS: 195

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaaagctgat ggacca                                                    16

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gaaagctgat ggacc                                                     15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaagctgatg gacca                                                     15

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaaagctgat ggac                                                      14

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaagctgatg gacc                                                      14
```

```
<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aagctgatgg acca                                                           14

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaaagctgat gga                                                            13

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaagctgatg gac                                                            13

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aagctgatgg acc                                                            13

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agctgatgga cca                                                            13

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gaaagctgat gg                                                             12
```

-continued

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaagctgatg ga                                                          12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aagctgatgg ac                                                          12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agctgatgga cc                                                          12

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gctgatggac ca                                                          12

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cagacttaaa gatggc                                                      16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cagaatccac tggtga                                                      16

<210> SEQ ID NO 18
<211> LENGTH: 16

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcactgccat tttagc                                                          16

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcactgccat tttag                                                           15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cactgccatt ttagc                                                           15

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcactgccat ttta                                                            14

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cactgccatt ttag                                                            14

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
actgccattt tagc                                                            14

<210> SEQ ID NO 24
<211> LENGTH: 13
<212> TYPE: DNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 24
gcactgccat ttt                                                         13

<210> SEQ ID NO 25
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cactgccatt tta                                                         13

<210> SEQ ID NO 26
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
actgccattt tag                                                         13

<210> SEQ ID NO 27
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctgccatttt agc                                                         13

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcactgccat tt                                                          12

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cactgccatt tt                                                          12

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
actgccattt ta                                                           12

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctgccatttt ag                                                           12

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgccatttta gc                                                           12

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtaatagcca agaatt                                                       16

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
actctgcttg tggtcc                                                       16

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
actctgcttg tggtc                                                        15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 36
ctctgcttgt ggtcc                                                   15

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
actctgcttg tggt                                                    14

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ctctgcttgt ggtc                                                    14

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tctgcttgtg gtcc                                                    14

<210> SEQ ID NO 40
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
actctgcttg tgg                                                     13

<210> SEQ ID NO 41
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctctgcttgt ggt                                                     13

<210> SEQ ID NO 42
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
```

```
tctgcttgtg gtc                                                        13

<210> SEQ ID NO 43
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctgcttgtgg tcc                                                        13

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
actctgcttg tg                                                         12

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctctgcttgt gg                                                         12

<210> SEQ ID NO 46
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tctgcttgtg gt                                                         12

<210> SEQ ID NO 47
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ctgcttgtgg tc                                                         12

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tgcttgtggt cc                                                         12
```

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccaccagctt ctacaa                                                     16

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gagtccaaag acagtt                                                     16

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
acccacttgg cagacc                                                     16

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gcacaaacaa tggaat                                                     16

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gcagctactc tttgga                                                     16

<210> SEQ ID NO 54
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctccctcagc ttcaat                                                     16

<210> SEQ ID NO 55

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcagtctcat tccaag                                                       16

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tatccaccag agtgaa                                                       16

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
catccatgag gtcctg                                                       16

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ccatcttgtg atccat                                                       16

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ccatcttgtg atcca                                                        15

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
catcttgtga tccat                                                        15

<210> SEQ ID NO 61
<211> LENGTH: 14
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 61
ccatcttgtg atcc                                                         14

<210> SEQ ID NO 62
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
catcttgtga tcca                                                         14

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
atcttgtgat ccat                                                         14

<210> SEQ ID NO 64
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccatcttgtg atc                                                          13

<210> SEQ ID NO 65
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
catcttgtga tcc                                                          13

<210> SEQ ID NO 66
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
atcttgtgat cca                                                          13

<210> SEQ ID NO 67
<211> LENGTH: 13
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 67
tcttgtgatc cat                                                          13

<210> SEQ ID NO 68
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccatcttgtg at                                                           12

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
catcttgtga tc                                                           12

<210> SEQ ID NO 70
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
atcttgtgat cc                                                           12

<210> SEQ ID NO 71
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tcttgtgatc ca                                                           12

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cttgtgatcc at                                                           12

<210> SEQ ID NO 73
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 73
aagcaagcaa agtcag                                                          16

<210> SEQ ID NO 74
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aagcaagcaa agtca                                                           15

<210> SEQ ID NO 75
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agcaagcaaa gtcag                                                           15

<210> SEQ ID NO 76
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aagcaagcaa agtc                                                            14

<210> SEQ ID NO 77
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
agcaagcaaa gtc                                                             13

<210> SEQ ID NO 78
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gcaagcaaag tcag                                                            14

<210> SEQ ID NO 79
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79

-continued aagcaagcaa agt    13

<210> SEQ ID NO 80
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
agcaagcaaa gtc    13

<210> SEQ ID NO 81
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gcaagcaaag tca    13

<210> SEQ ID NO 82
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
caagcaaagt cag    13

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aagcaagcaa ag    12

<210> SEQ ID NO 84
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
agcaagcaaa gt    12

<210> SEQ ID NO 85
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gcaagcaaag tc    12

<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
caagcaaagt ca                                                           12

<210> SEQ ID NO 87
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aagcaaagtc ag                                                           12

<210> SEQ ID NO 88
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gaaattgctg tagcag                                                       16

<210> SEQ ID NO 89
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gaaattgctg tagca                                                        15

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aaattgctgt agcag                                                        15

<210> SEQ ID NO 91
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gaaattgctg tagc                                                         14

```
<210> SEQ ID NO 92
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aaattgctgt agca                                                         14

<210> SEQ ID NO 93
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aattgctgta gcag                                                         14

<210> SEQ ID NO 94
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gaaattgctg tag                                                          13

<210> SEQ ID NO 95
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aaattgctgt agc                                                          13

<210> SEQ ID NO 96
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aattgctgta gca                                                          13

<210> SEQ ID NO 97
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
attgctgtag cag                                                          13

<210> SEQ ID NO 98
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gaaattgctg ta                                                              12

<210> SEQ ID NO 99
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aaattgctgt ag                                                              12

<210> SEQ ID NO 100
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aattgctgta gc                                                              12

<210> SEQ ID NO 101
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
attgctgtag ca                                                              12

<210> SEQ ID NO 102
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ttgctgtagc ag                                                              12

<210> SEQ ID NO 103
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gtgttctaca ccatta                                                          16

<210> SEQ ID NO 104
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 104
gtgttctaca ccatt                                                          15

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tgttctacac catta                                                          15

<210> SEQ ID NO 106
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtgttctaca ccat                                                           14

<210> SEQ ID NO 107
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tgttctacac catt                                                           14

<210> SEQ ID NO 108
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gttctacacc atta                                                           14

<210> SEQ ID NO 109
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gtgttctaca cca                                                            13

<210> SEQ ID NO 110
<211> LENGTH: 13
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 110
tgttctacac cat                                                        13

<210> SEQ ID NO 111
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gttctacacc att                                                        13

<210> SEQ ID NO 112
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ttctacacca tta                                                        13

<210> SEQ ID NO 113
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gtgttctaca cc                                                         12

<210> SEQ ID NO 114
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tgttctacac ca                                                         12

<210> SEQ ID NO 115
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gttctacacc at                                                         12

<210> SEQ ID NO 116
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 116
ttctacacca tt                                                          12

<210> SEQ ID NO 117
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tctacaccat ta                                                          12

<210> SEQ ID NO 118
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
aacatgaaat agatcc                                                      16

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aacatgaaat agatc                                                       15

<210> SEQ ID NO 120
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
acatgaaata gatcc                                                       15

<210> SEQ ID NO 121
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
aacatgaaat agat                                                        14

<210> SEQ ID NO 122
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
```

-continued

```
acatgaaata gatc                                                    14

<210> SEQ ID NO 123
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
catgaaatag atcc                                                    14

<210> SEQ ID NO 124
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
aacatgaaat aga                                                     13

<210> SEQ ID NO 125
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
acatgaaata gat                                                     13

<210> SEQ ID NO 126
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
catgaaatag atc                                                     13

<210> SEQ ID NO 127
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
atgaaataga tcc                                                     13

<210> SEQ ID NO 128
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
aacatgaaat ag                                                      12
```

-continued

```
<210> SEQ ID NO 129
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
acatgaaata ga                                                            12

<210> SEQ ID NO 130
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
catgaaatag at                                                            12

<210> SEQ ID NO 131
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
atgaaataga tc                                                            12

<210> SEQ ID NO 132
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tgaaatagat cc                                                            12

<210> SEQ ID NO 133
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
```

```
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 133
gaaagctgat ggacca                                                  16

<210> SEQ ID NO 134
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
```

```
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 134
cagacttaaa gatggc                                                16

<210> SEQ ID NO 135
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
```

```
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 135
cagaatccac tggtga                                              16

<210> SEQ ID NO 136
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
```

```
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 136
gcactgccat tttagc                                                    16

<210> SEQ ID NO 137
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
```

```
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 137
gtaatagcca agaatt                                                     16

<210> SEQ ID NO 138
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
```

```
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 138
actctgcttg tggtcc                                                     16

<210> SEQ ID NO 139
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
```

```
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 139
ccaccagctt ctacaa                                              16

<210> SEQ ID NO 140
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
```

```
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 140
gagtccaaag acagtt                                               16

<210> SEQ ID NO 141
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
```

```
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 141
acccacttgg cagacc                                                       16

<210> SEQ ID NO 142
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
```

-continued

```
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 142
gcacaaacaa tggaat                                                    16

<210> SEQ ID NO 143
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
```

```
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 143
gcagctactc tttgga                                                  16

<210> SEQ ID NO 144
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
```

```
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 144
ctccctcagc ttcaat                                              16

<210> SEQ ID NO 145
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
```

```
-continued

<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 145
gcagtctcat tccaag                                                    16

<210> SEQ ID NO 146
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
```

-continued

```
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 146
tatccaccag agtgaa                                                    16

<210> SEQ ID NO 147
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
<221> NAME/KEY: misc_feature
```

```
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 147
catccatgag gtcctg                                                    16

<210> SEQ ID NO 148
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
<220> FEATURE:
```

```
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 148
ccatcttgtg atccat                                             16

<210> SEQ ID NO 149
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Nucleoside analogue monomer
```

```
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 149
aagcaagcaa agtcag                                                 16

<210> SEQ ID NO 150
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
```

```
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 150
gaaattgctg tagcag                                                   16

<210> SEQ ID NO 151
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 151
gtgttctaca ccatta                                                      16

<210> SEQ ID NO 152
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(3)
<223> OTHER INFORMATION: Nucleoside analogue monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Nucleoside analogue monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 152
aacatgaaat agatcc                                              16

<210> SEQ ID NO 153
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: modified_base
<222> LOCATION: (14)..(15)
<223> OTHER INFORMATION: 5-methylcytosine
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 153
gaaagctgat ggacca                                                     16

<210> SEQ ID NO 154
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: modified_base
<222> LOCATION: (1)..(1)
<223> OTHER INFORMATION: 5-methylcytosine
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage
<220> FEATURE:
<221> NAME/KEY: modified_base
<222> LOCATION: (16)..(16)
```

<223> OTHER INFORMATION: 5-methylcytosine

<400> SEQUENCE: 154
cagacttaaa gatggc 16

<210> SEQ ID NO 155
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: modified_base
<222> LOCATION: (1)..(1)
<223> OTHER INFORMATION: 5-methylcytosine
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature

```
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 155
cagaatccac tggtga                                                  16

<210> SEQ ID NO 156
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)..(2)
<223> OTHER INFORMATION: 5-methylcytosine
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
```

```
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage
<220> FEATURE:
<221> NAME/KEY: modified_base
<222> LOCATION: (16)..(16)
<223> OTHER INFORMATION: 5-methylcytosine

<400> SEQUENCE: 156
gcactgccat tttagc                                                    16

<210> SEQ ID NO 157
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
```

```
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 157
gtaatagcca agaatt                                                      16

<210> SEQ ID NO 158
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)..(2)
<223> OTHER INFORMATION: 5-methylcytosine
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
```

-continued

```
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: modified_base
<222> LOCATION: (15)..(16)
<223> OTHER INFORMATION: 5-methylcytosine
<220> FEATURE:
<221> NAME/KEY: misc_feature
<222> LOCATION: (15)..(16)
<223> OTHER INFORMATION: Phosphorothioate linkage

<400> SEQUENCE: 158
actctgcttg tggtcc                                                       16

<210> SEQ ID NO 159
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: modified_base
<222> LOCATION: (1)..(2)
<223> OTHER INFORMATION: 5-methylcytosine
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
```

```
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: modified_base
<222> LOCATION: (14)..(14)
<223> OTHER INFORMATION: 5-methylcytosine
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 159
ccaccagctt ctacaa                                                   16

<210> SEQ ID NO 160
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
```

```
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 160
gagtccaaag acagtt                                              16

<210> SEQ ID NO 161
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)..(3)
<223> OTHER INFORMATION: 5-methylcytosine
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
```

```
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: modified_base
<222> LOCATION: (15)..(16)
<223> OTHER INFORMATION: 5-methylcytosine
<220> FEATURE:
<221> NAME/KEY: misc_feature
<222> LOCATION: (15)..(16)
<223> OTHER INFORMATION: Phosphorothioate linkage

<400> SEQUENCE: 161
acccacttgg cagacc                                                    16

<210> SEQ ID NO 162
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)..(2)
<223> OTHER INFORMATION: 5-methylcytosine
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
```

-continued

```
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 162
gcacaaacaa tggaat                                                     16

<210> SEQ ID NO 163
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)..(2)
<223> OTHER INFORMATION: 5-methylcytosine
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
```

<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 163
gcagctactc tttgga                                                       16

<210> SEQ ID NO 164
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: modified_base
<222> LOCATION: (1)..(1)
<223> OTHER INFORMATION: 5-methylcytosine
<220> FEATURE:
<221> NAME/KEY: misc_feature
<222> LOCATION: (1)..(2)
<223> OTHER INFORMATION: Phosphorothioate linkage
<220> FEATURE:

```
<221> NAME/KEY: misc_feature
<222> LOCATION: (2)..(3)
<223> OTHER INFORMATION: Phosphorothioate linkage
<220> FEATURE:
<221> NAME/KEY: modified_base
<222> LOCATION: (3)..(3)
<223> OTHER INFORMATION: 5-methylcytosine
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 164
ctccctcagc ttcaat                                                  16

<210> SEQ ID NO 165
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
```

```
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)..(2)
<223> OTHER INFORMATION: 5-methylcytosine
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 165
gcagtctcat tccaag                                                    16

<210> SEQ ID NO 166
<211> LENGTH: 16
<212> TYPE: DNA
<213> ORGANISM: Artificial Sequence
<220> FEATURE:
<223> OTHER INFORMATION: Description of Artificial Sequence: Synthetic
```

```
              oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 166
tatccaccag agtgaa                                                    16

<210> SEQ ID NO 167
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: modified_base
<222> LOCATION: (1)..(1)
<223> OTHER INFORMATION: 5-methylcytosine
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: modified_base
<222> LOCATION: (14)..(14)
<223> OTHER INFORMATION: 5-methylcytosine
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 167
```

```
catccatgag gtcctg                                                    16
```

<210> SEQ ID NO 168
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: modified_base
<222> LOCATION: (1)..(2)
<223> OTHER INFORMATION: 5-methylcytosine
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: modified_base
<222> LOCATION: (14)..(14)
<223> OTHER INFORMATION: 5-methylcytosine
<220> FEATURE:

```
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 168
ccatcttgtg atccat                                              16

<210> SEQ ID NO 169
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
```

```
<220> FEATURE:
<221> NAME/KEY: modified_base
<222> LOCATION: (14)..(14)
<223> OTHER INFORMATION: 5-methylcytosine
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 169
aagcaagcaa agtcag                                                     16

<210> SEQ ID NO 170
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
```

-continued

```
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: modified_base
<222> LOCATION: (14)..(14)
<223> OTHER INFORMATION: 5-methylcytosine
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 170
gaaattgctg tagcag                                                 16

<210> SEQ ID NO 171
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
```

```
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 171
gtgttctaca ccatta                                                       16

<210> SEQ ID NO 172
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: modified_base
<222> LOCATION: (3)..(3)
<223> OTHER INFORMATION: 5-methylcytosine
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
```

```
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(16)
<223> OTHER INFORMATION: Beta-D-oxy-LNA monomer
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: modified_base
<222> LOCATION: (15)..(16)
<223> OTHER INFORMATION: 5-methylcytosine
<220> FEATURE:
<221> NAME/KEY: misc_feature
<222> LOCATION: (15)..(16)
<223> OTHER INFORMATION: Phosphorothioate linkage

<400> SEQUENCE: 172
aacatgaaat agatcc                                                   16

<210> SEQ ID NO 173
<211> LENGTH: 3697
<212> TYPE: DNA
<213> ORGANISM: Homo sapiens

<400> SEQUENCE: 173
cccacgcgtc cgggcagcag cgttggcccg gccccgggag cggagagcga ggggaggcgg    60
agacggagga aggtctgagg agcagcttca gtccccgccg agccgccacc gcaggtcgag   120
gacggtcgga ctcccgcggc gggaggagcc tgttcccctg agggtatttg aagtatacca   180
tacaactgtt ttgaaaatcc agcgtggaca atggctactc aagctgattt gatggagttg   240
gacatggcca tggaaccaga cagaaaagcg gctgttagtc actggcagca acagtcttac   300
ctggactctg gaatccattc tggtgccact accacagctc cttctctgag tggtaaaggc   360
aatcctgagg aagaggatgt ggataccctcc caagtcctgt atgagtggga caggggattt   420
tctcagtcct tcactcaaga acaagtagct gatattgatg acagtatgc aatgactcga   480 gctcagaggg tacgagctgc tatgttccct gagacattag atgagggcat gcagatccca   540
tctacacagt ttgatgctgc tcatcccact aatgtccagc gtttggctga accatcacag   600
atgctgaaac atgcagttgt aaacttgatt aactatcaag atgatgcaga acttgccaca   660
cgtgcaatcc ctgaactgac aaaactgcta aatgacgagg accaggtggt ggttaataag   720
gctgcagtta tggtccatca gctttctaaa aaggaagctt ccagacacgc tatcatgcgt   780
tctcctcaga tggtgtctgc tattgtacgt accatgcaga atacaaatga tgtagaaaca   840
gctcgttgta ccgctgggac cttgcataac ctttcccatc atcgtgaggg cttactggcc   900
atctttaagt ctggaggcat tcctgccctg gtgaaaatgc ttggttcacc agtggattct   960
gtgttgtttt atgccattac aactctccac aaccttttat tacatcaaga aggagctaaa  1020
atggcagtgc gtttagctgg tgggctgcag aaaatggttg ccttgctcaa caaaacaaat  1080
gttaaattct tggctattac gacagactgc cttcaaattt tagcttatgg caaccaagaa  1140
agcaagctca tcatactggc tagtggtgga ccccaagctt tagtaaatat aatgaggacc  1200
```

```
tatacttacg aaaaactact gtggaccaca agcagagtgc tgaaggtgct atctgtctgc    1260
tctagtaata agccggctat tgtagaagct ggtggaatgc aagctttagg acttcacctg    1320
acagatccaa gtcaacgtct tgttcagaac tgtctttgga ctctcaggaa tctttcagat    1380
gctgcaacta acaggaagg  gatggaaggt ctccttggga ctcttgttca gcttctgggt    1440
tcagatgata taaatgtggt cacctgtgca gctggaattc tttctaacct cacttgcaat    1500
aattataaga acaagatgat ggtctgccaa gtgggtggta tagaggctct tgtgcgtact    1560
gtccttcggg ctggtgacag ggaagacatc actgagcctg ccatctgtgc tcttcgtcat    1620
ctgaccagcc gacaccaaga agcagagatg gcccagaatg cagttcgcct tcactatgga    1680
ctaccagttg tggttaagct cttacaccca ccatcccact ggcctctgat aaaggctact    1740
gttggattga ttcgaaatct tgcccttttgt cccgcaaatc atgcaccttt gcgtgagcag    1800
ggtgccattc cacgactagt tcagttgctt gttcgtgcac atcaggatac ccagcgccgt    1860
acgtccatgg gtgggacaca gcagcaattt gtggagggggg tccgcatgga agaaatagtt    1920
gaaggttgta ccggagccct tcacatccta gctcgggatg ttcacaaccg aattgttatc    1980
agaggactaa ataccattcc attgtttgtg cagctgcttt attctcccat tgaaaacatc    2040
caaagagtag ctgcagggggt cctctgtgaa cttgctcagg acaaggaagc tgcagaagct    2100
attgaagctg agggagccac agctcctctg acagagttac ttcactctag gaatgaaggt    2160
gtggcgacat atgcagctgc tgttttgttc cgaatgtctg aggacaagcc acaagattac    2220
aagaaacggc tttcagttga gctgaccagc tctctcttca gaacagagcc aatggcttgg    2280
aatgagactg ctgatcttgg acttgatatt ggtgcccagg gagaacccct tggatatcgc    2340
caggatgatc ctagctatcg ttcttttcac tctggtggat atggccagga tgccttgggt    2400
atggacccca tgatggaaca tgagatgggt ggccaccacc ctggtgctga ctatccagtt    2460
gatgggctgc cagatctggg gcatgcccag gacctcatgg atgggctgcc tccaggtgac    2520
agcaatcagc tggcctggtt tgatactgac ctgtaaatca tcctttaggt aagaagtttt    2580
aaaaagccag tttgggtaaa atacttttac tctgcctaca gaacttcaga aagacttggt    2640 tggtaggggtg ggagtggttt aggctatttg taaatctgcc acaaaaacag gtatatactt    2700
tgaaaggaga tgtcttggaa cattggaatg ttctcagatt tctggttgtt atgtgatcat    2760
gtgtggaagt tattaacttt aatgtttttt gccacagctt ttgcaactta atactcaaat    2820
gagtaacatt tgctgtttta aacattaata gcagcctttc tctctttata cagctgtatt    2880
gtctgaactt gcattgtgat tggcctgtag agttgctgag agggctcgag gggtgggctg    2940
gtatctcaga aagtgcctga cacactaacc aagctgagtt tcctatggga acaattgaag    3000 taaactttttt gttctggtcc tttttggtcg aggagtaaca atacaaatgg attttgggag    3060
tgactcaaga agtgaagaat gcacaagaat ggatcacaag atggaattta gcaaaccta    3120 gccttgcttg ttaaaatttt tttttttttt tttaagaat atctgtaatg gtactgactt    3180
tgcttgcttt gaagtagctc tttttttttt tttttttttt ttttttttgc agtaactgtt    3240
ttttaagtct ctcgtagtgt taagttatag tgaatactgc tacagcaatt tctaattttt    3300
aagaattgag taatggtgta gaacactaat taattcataa tcactctaat taattgtaat    3360
ctgaataaag tgtaacaatt gtgtagcctt tttgtataaa atagacaaat agaaaatggt    3420
ccaattagtt tccttttttaa tatgcttaaa ataagcaggt ggatctattt catgtttttg    3480
atcaaaaact atttgggata tgtatgggta gggtaaatca gtaagaggtg ttatttggaa    3540
ccttgttttg gacagtttac cagttgcctt ttatcccaaa gttgttgtaa cctgctgtga    3600
```

```
tacgatgctt caagagaaaa tgcggttata aaaaatggtt cagaattaaa cttttaattc    3660
attcaaaaaa aaaaaaaaaa aaaaaaaaaa aaaaaa                              3697
```

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174

```
tttagaaagc tgatggacca taac                                             24
```

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175

```
cctccagact taaagatggc cagt                                             24
```

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176

```
aacacagaat ccactggtga acca                                             24
```

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177

```
aaacgcactg ccattttagc tcct                                             24
```

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178

```
tgtcgtaata gccaagaatt taac                                             24
```

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179

-continued cagcactctg cttgtggtcc acag                                          24

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cattccacca gcttctacaa tagc                                          24

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ctgagagtcc aaagacagtt ctga                                          24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
taccacccac ttggcagacc atca                                          24

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
agctgcacaa acaatggaat ggta                                          24

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ccctgcagct actctttgga tgtt                                          24

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
gtggctccct cagcttcaat agct                                          24

```
<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
atcagcagtc tcattccaag ccat                                              24

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gccatatcca ccagagtgaa aaga                                              24

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
agcccatcca tgaggtcctg ggca                                              24

<210> SEQ ID NO 189
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aattccatct tgtgatccat tctt                                              24

<210> SEQ ID NO 190
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
ttcaaagcaa gcaaagtcag tacc                                              24

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
attagaaatt gctgtagcag tatt                                              24

<210> SEQ ID NO 192
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
attagtgttc tacaccatta ctca                                              24

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
caaaaacatg aaatagatcc acct                                              24

<210> SEQ ID NO 194
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA monomer
<220> FEATURE:
<221> NAME/KEY: modified_base
<222> LOCATION: (1)..(1)
<223> OTHER INFORMATION: 5-methylcytosine
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
```

-continued

```
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: modified_base
<222> LOCATION: (13)..(15)
<223> OTHER INFORMATION: Beta-D-oxy-LNA monomer
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage

<400> SEQUENCE: 194
cgtcagtatg cgaatc                                                      16

<210> SEQ ID NO 195
<211> LENGTH: 3720
<212> TYPE: DNA
<213> ORGANISM: Homo sapiens

<400> SEQUENCE: 195
aggatacagc ggcttctgcg cgacttataa gagctccttg tgcggcgcca ttttaagcct      60
ctcggtctgt ggcagcagcg ttggcccggc cccgggagcg gagagcgagg ggaggcggag     120
acggaggaag gtctgaggag cagcttcagt ccccgccgag ccgccaccgc aggtcgagga     180
cggtcggact cccgcggcgg gaggagcctg ttccctgag ggtatttgaa gtataccata      240
caactgtttt gaaaatccag cgtggacaat ggctactcaa gctgatttga tggagttgga     300
catggccatg gaaccagaca gaaaagcggc tgttagtcac tggcagcaac agtcttacct     360
ggactctgga atccattctg gtgccactac cacagctcct tctctgagtg gtaaaggcaa     420
tcctgaggaa gaggatgtgg atacctccca gtcctgtat gagtgggaac agggatttc      480 tcagtccttc actcaagaac aagtagctga tattgatgga cagtatgcaa tgactcgagc     540
tcagagggta cgagctgcta tgttccctga gacattagat gagggcatgc agatcccatc     600
tacacagttt gatgctgctc atcccactaa tgtccagcgt ttggctgaac catcacagat     660
gctgaaacat gcagttgtaa acttgattaa ctatcaagat gatgcagaac ttgccacacg     720
tgcaatccct gaactgacaa aactgctaaa tgacgaggac caggtggtgg ttaataaggc     780
tgcagttatg gtccatcagc tttctaaaaa ggaagcttcc agacacgcta tcatgcgttc     840
tcctcagatg gtgtctgcta ttgtacgtac catgcagaat acaaatgatg tagaaacagc     900
tcgttgtacc gctgggacct tgcataacct ttcccatcat cgtgagggct tactggccat     960
ctttaagtct ggaggcattc ctgccctggt gaaaatgctt ggttcaccag tggattctgt    1020 gttgtttat gccattacaa ctctccacaa ccttttatta catcaagaag gagctaaaat     1080
ggcagtgcgt ttagctggtg ggctgcagaa aatggttgcc ttgctcaaca aaacaaatgt    1140
taaattcttg gctattacga cagactgcct tcaaatttta gcttatgca accaagaaag    1200 caagctcatc atactggcta gtggtggacc ccaagcttta gtaaatataa tgaggaccta    1260
tacttacgaa aaactactgt ggaccacaag cagagtgctg aaggtgctat ctgtctgctc    1320
```

```
tagtaataag ccggctattg tagaagctgg tggaatgcaa gctttaggac ttcacctgac    1380
agatccaagt caacgtcttg ttcagaactg tctttggact ctcaggaatc tttcagatgc    1440
tgcaactaaa caggaaggga tggaaggtct ccttgggact cttgttcagc ttctgggttc    1500
agatgatata aatgtggtca cctgtgcagc tggaattctt tctaacctca cttgcaataa    1560
ttataagaac aagatgatgg tctgccaagt gggtggtata gaggctcttg tgcgtactgt    1620
ccttcgggct ggtgacaggg aagacatcac tgagcctgcc atctgtgctc ttcgtcatct    1680
gaccagccga caccaagaag cagagatggc ccagaatgca gttcgccttc actatggact    1740
accagttgtg gttaagctct tacacccacc atcccactgg cctctgataa aggctactgt    1800
tggattgatt cgaaatcttg cccctttgtcc cgcaaatcat gcacctttgc gtgagcaggg    1860
tgccattcca cgactagttc agttgcttgt tcgtgcacat caggataccc agcgccgtac    1920
gtccatgggt gggacacagc agcaatttgt ggaggggtc cgcatggaag aaatagttga    1980
aggttgtacc ggagcccttc acatcctagc tcgggatgtt cacaaccgaa ttgttatcag    2040
aggactaaat accattccat gttttgtgca gctgctttat tctcccattg aaaacatcca    2100
aagagtagct gcaggggtcc tctgtgaact tgctcaggac aaggaagctg cagaagctat    2160
tgaagctgag ggagccacag ctcctctgac agagttactt cactctagga atgaaggtgt    2220
ggcgacatat gcagctgctg ttttgttccg aatgtctgag gacaagccac aagattacaa    2280
gaaacggctt tcagttgagc tgaccagctc tctcttcaga acagagccaa tggcttggaa    2340
tgagactgct gatcttggac ttgatattgg tgcccaggga gaaccccttg gatatcgcca    2400
ggatgatcct agctatcgtt cttttcactc tggtggatat ggccaggatg ccttgggtat    2460
ggaccccatg atggaacatg agatgggtgg ccaccaccct ggtgctgact atccagttga    2520
tgggctgcca gatctggggc atgcccagga cctcatggat gggctgcctc caggtgacag    2580
caatcagctg gcctggtttg atactgacct gtaaatcatc ctttaggtaa gaagttttaa    2640
aaagccagtt tgggtaaaat acttttactc tgcctacaga acttcagaaa gacttggttg    2700
gtagggtggg agtggtttag gctatttgta aatctgccac aaaaacaggt atatactttg    2760
aaaggagatg tcttggaaca ttggaatgtt ctcagatttc tggttgttat gtgatcatgt    2820
gtggaagtta ttaacttaa tgttttttgc cacagctttt gcaacttaat actcaaatga    2880
gtaacatttg ctgtttaaa cattaatagc agcctttctc tctttataca gctgtattgt    2940
ctgaacttgc attgtgattg gcctgtagag ttgctgagag ggctcgaggg gtgggctggt    3000
atctcagaaa gtgcctgaca cactaaccaa gctgagtttc ctatgggaac aattgaagta    3060
aacttttgt tctggtcctt tttggtcgag gagtaacaat acaaatggat tttgggagtg    3120
actcaagaag tgaagaatgc acaagaatgg atcacaagat ggaatttatc aaaccctagc    3180
cttgcttgtt aaatttttt tttttttttt ttaagaatat ctgtaatggt actgactttg    3240
cttgctttga gtagctctt tttttttttt tttttttttt tttgcagtaa ctgtttttta    3300
agtctctcgt agtgttaagt tatagtgaat actgctacag caatttctaa ttttttaagaa    3360
ttgagtaatg gtgtagaaca ctaattcata atcactctaa ttaattgtaa tctgaataaa    3420
gtgtaacaat tgtgtagcct ttttgtataa aatagacaaa tagaaaatgg tccaattagt    3480
ttccttttta atatgcttaa aataagcagg tggatctatt tcatgttttt gatcaaaaac    3540
tatttgggat atgtatgggt agggtaaatc agtaagaggt gttatttgga accttgtttt    3600
ggacagttta ccagttgcct tttatcccaa agttgttgta acctgctgtg atacgatgct    3660
tcaagagaaa atgcggttat aaaaaatggt tcagaattaa acttttaatt cattcgattg    3720
```